US012268498B2

(12) United States Patent
Mannino et al.

(10) Patent No.: US 12,268,498 B2
(45) Date of Patent: Apr. 8, 2025

(54) SYSTEMS AND METHODS FOR QUANTITATIVE DIAGNOSIS OF ANEMIA

(71) Applicants: EMORY UNIVERSITY, Atlanta, GA (US); CHILDREN'S HEALTHCARE OF ATLANTA, INC., Atlanta, GA (US); GEORGIA TECH RESEARCH CORPORATION, INC., Atlanta, GA (US); Sanguina, Inc, Peachtree Corners, GA (US)

(72) Inventors: Robert Mannino, Atlanta, GA (US); Wilbur Lam, Atlanta, GA (US); Gari Clifford, Atlanta, GA (US); Erika Tyburski, Norcross, GA (US)

(73) Assignees: EMORY UNIVERSITY, Atlanta, GA (US); CHILDREN'S HEALTHCARE OF ATLANTA, INC., Atlanta, GA (US); GEORGIA TECH RESEARCH CORPORATION, INC., Peachtree Corners, GA (US); Sanguina, Inc., Peachtree Corners, GA (US)

( * ) Notice: Subject to any disclaimer, the term of this patent is extended or adjusted under 35 U.S.C. 154(b) by 697 days.

(21) Appl. No.: 17/291,215

(22) PCT Filed: Nov. 5, 2019

(86) PCT No.: PCT/US2019/059742
§ 371 (c)(1),
(2) Date: May 4, 2021

(87) PCT Pub. No.: WO2020/096999
PCT Pub. Date: May 14, 2020

(65) Prior Publication Data
US 2021/0361195 A1 Nov. 25, 2021

Related U.S. Application Data

(60) Provisional application No. 62/755,930, filed on Nov. 5, 2018.

(51) Int. Cl.
A61B 5/00 (2006.01)
A61B 5/103 (2006.01)
(Continued)

(52) U.S. Cl.
CPC .......... *A61B 5/1455* (2013.01); *A61B 5/1032* (2013.01); *A61B 5/14535* (2013.01);
(Continued)

(58) Field of Classification Search
CPC .... A61B 5/14535; A61B 5/449; A61B 5/6898
See application file for complete search history.

(56) References Cited

U.S. PATENT DOCUMENTS 6,104,939 A 8/2000 Groner et al.
2003/0002722 A1 1/2003 Jay et al.
(Continued)

OTHER PUBLICATIONS

Indi, T. and Gunge, Y. "Early Stage Disease Diagnosis System Using Human Nail Image Processing." International Journal of Information Technology and Computer Science. 8. 30-35. (Year: 2016).*

(Continued)

*Primary Examiner* — Amal Aly Farag
(74) *Attorney, Agent, or Firm* — Meunier Carlin & Curfman LLC

(57) ABSTRACT

A smartphone-based hemoglobin (Hgb) assessment application quantitatively analyzes pallor in patient-sourced photos using image analysis algorithms to enable a noninvasive, accurate quantitative smartphone app for detecting anemia. A user takes a photo of his/her fingernail beds using the app and receives an accurate displayed Hgb level. Since fingernails do not contain melanocytes, the primary source of color of these anatomical features is blood Hgb. At the same time, quality control software minimizes the impact of common fingernail irregularities (e.g. leukonychia and cam- (Continued)

era flash reflection) on Hgb level measurement. Metadata recorded upon capturing the image is leveraged for determining a users' Hgb level thereby eliminating the need for external equipment. A personalized calibration of image data with measured Hgb levels improves the accuracy of the application.

19 Claims, 24 Drawing Sheets

(51) Int. Cl.
  *A61B 5/145* (2006.01)
  *A61B 5/1455* (2006.01)
  *G06T 7/11* (2017.01)
  *G06T 7/90* (2017.01)
  *H04N 23/74* (2023.01)

(52) U.S. Cl.
  CPC ............ *A61B 5/449* (2013.01); *A61B 5/6898* (2013.01); *A61B 5/7435* (2013.01); *A61B 5/748* (2013.01); *G06T 7/11* (2017.01); *G06T 7/90* (2017.01); *H04N 23/74* (2023.01); *A61B 2560/0223* (2013.01); *A61B 2576/02* (2013.01); *G06T 2200/24* (2013.01); *G06T 2207/10152* (2013.01); *G06T 2207/20081* (2013.01); *G06T 2207/30104* (2013.01)

(56) References Cited

U.S. PATENT DOCUMENTS

| | | | |
|---|---|---|---|
| 2007/0255115 A1* | 11/2007 | Anglin | G16H 10/60 600/300 |
| 2009/0267893 A1* | 10/2009 | Kato | G06F 3/03547 348/143 |
| 2011/0082711 A1* | 4/2011 | Poeze | A61B 5/6825 600/300 |
| 2012/0265041 A1* | 10/2012 | Yamaguchi | A61B 1/045 600/109 |
| 2015/0044098 A1 | 2/2015 | Smart et al. | |
| 2016/0089062 A1* | 3/2016 | Sivathanu | A61B 3/145 600/479 |
| 2017/0311871 A1* | 11/2017 | Kikuchi | A61B 5/0075 |
| 2018/0012365 A1 | 1/2018 | Chefd'hotel et al. | |
| 2018/0125610 A1* | 5/2018 | Carrier, Jr. | H04N 5/272 |

OTHER PUBLICATIONS

Wang, E.J., Li, W., Hawkins, D., Gernsheimer, T., et al. HemaApp: Noninvasive Blood Screening of Hemoglobin Using Smartphone Cameras. Proceedings of the 2016 ACM International Joint Conference on Pervasive and Ubiquitous Computing (UbiComp '16) (Year: 2016).*
International Search Report and Written Opinion for International Application No. PCT/US2019/059742 dated Jan. 21, 2020.
Sanguina, "Over the counter Development" Oct. 10, 2019, 1 page.
International Preliminary Report on Patentability issued for Application No. PCT/US2019/059742, dated May 20, 2021.

* cited by examiner

CBC MEASURED Hgb LEVEL: 15.3 g/dL
MEASURED Hgb LEVEL WITH QUALITY CONTROL: 14.7 g/dL
MEASURED Hgb LEVEL WITHOUT QUALITY CONTROL: 12.8 g/dL

SYSTEMS AND METHODS FOR QUANTITATIVE DIAGNOSIS OF ANEMIA

CROSS-REFERENCE TO RELATED APPLICATIONS

This application is a national stage application filed under 35 U.S.C. § 371 of PCT/US2019/059742 filed Nov. 5, 2019, which claims the benefit of U.S. Provisional Patent Application Ser. No. 62/755,930 filed Nov. 5, 2018, the disclosures of which are expressly incorporated herein by reference.

BACKGROUND

Although smartphone-based technologies have the potential to change how healthcare is delivered by enabling remote diagnoses, these technologies have yet to effectively replace other, invasive techniques, including blood-based testing, which remains a major cornerstone of disease diagnosis in modern medicine. Indeed, many smartphone-based technologies require smartphone attachments (purchased separately from the smartphone, along with an app). While such attachments may allow for remote diagnosis and analysis by a smartphone, the additional cost and complexity of multi-part systems may prevent broader adoption of these potentially disruptive technologies.

Therefore there exists a need for a completely non-invasive, smartphone-based diagnostics technology that may replace common laboratory tests, including blood-based clinical laboratory tests.

SUMMARY

A first aspect of the disclosure includes a system for analyzing an image for estimating hemoglobin levels. The system comprising at least one processor configured to receive an image of one or more fingernail beds of a user from a camera with a flash functionality activated. The processor is further configured to receive an indication of one or more regions of interest on the image, the one or more regions of interest at least partially including the one or more fingernail beds. The processor is further configured to quantitatively analyze pallor of the one or more fingernail beds in the one or more regions of interest to determine the user's approximate hemoglobin (Hgb) level by determining pixel intensity for each of the one or more regions of interest. Quantitatively analyzing the pallor of fingernail beds further includes averaging pixel intensity from color channels across each of the one or more regions of interest. Quantitatively analyzing the pallor of fingernail beds further includes transforming the average pixel intensity from the color channels into a value that correlates with the user's approximate Hgb level. The processor is further configured to output for display the user's approximate Hgb level.

In some implementations of the first aspect of the disclosure, the at least one processor is further configured to receive the indication of the one or more regions of interest via input by the user and automatically display a visual indication of the one or more regions of interest.

In some implementations of the first aspect of the disclosure, the input by the user comprises the user tapping the image to indicate the one or more regions of interest.

In some implementations of the first aspect of the disclosure, the visual indication of the one or more regions of interest comprise one or more boxes encompassing each of the one or more regions of interest.

In some implementations of the first aspect of the disclosure, the one or more regions of interest include an area of approximately 10 $mm^2$.

In some implementations of the first aspect of the disclosure, the one or more regions of interest consist of one or more portions of the one or more fingernail beds.

In some implementations of the first aspect of the disclosure, the at least one processor is further configured to receive the indication of the one or more regions of interest automatically from a third-party computing system.

In some implementations of the first aspect of the disclosure, the at least one processor is further configured to receive the indication of the one or more regions of interest automatically from a remote server.

In some implementations of the first aspect of the disclosure, the remote server determines the one or more regions of interest via a machine learning algorithm.

In some implementations of the first aspect of the disclosure, the at least one processor is further configured to determine the one or more regions of interest automatically.

In some implementations of the first aspect of the disclosure, the at least one processor determines the one or more regions of interest via a machine learning algorithm.

In some implementations of the first aspect of the disclosure, the system receives the image of the one or more fingernail beds of the user and quantitatively analyzes the pallor of the one or more fingernail beds in the one or more regions of interest without the use of external hardware physically coupled to the system.

In some implementations of the first aspect of the disclosure, the determining pixel intensity for each of the one or more regions of interest comprises extracting color data from the image.

In some implementations of the first aspect of the disclosure, the transforming the average pixel intensity from the color channels into the value that correlates to the user's approximate Hgb level comprises determining metadata associated with the image and the camera and adjusting the value based on the metadata.

In some implementations of the first aspect of the disclosure, the at least one processor is further configured to exclude areas including leukonychia and/or camera flash reflection from the one or more regions of interest.

In some implementations of the first aspect of the disclosure, the transforming the average pixel intensity from the color channels into the value that correlates to the user's approximate Hgb level comprises using linear regression to correct for variations in the average pixel intensity.

In some implementations of the first aspect of the disclosure, the user's approximate Hgb level is an approximate complete blood count (CBC) Hgb level.

In some implementations of the first aspect of the disclosure, the at least one processor is configured to save the user's approximate Hgb level in a text file.

In some implementations of the first aspect of the disclosure, the quantitatively analyzing the pallor of the one or more fingernail beds in the one or more regions of interest to determine the user's approximate Hgb level comprises excluding pixel intensity values outside of a particular range.

In some implementations of the first aspect of the disclosure, the camera is on a mobile device and the at least one processor is further configured to access the camera and automatically activate flash functionality associated with the camera to take the image of one or more fingernail beds of the user.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
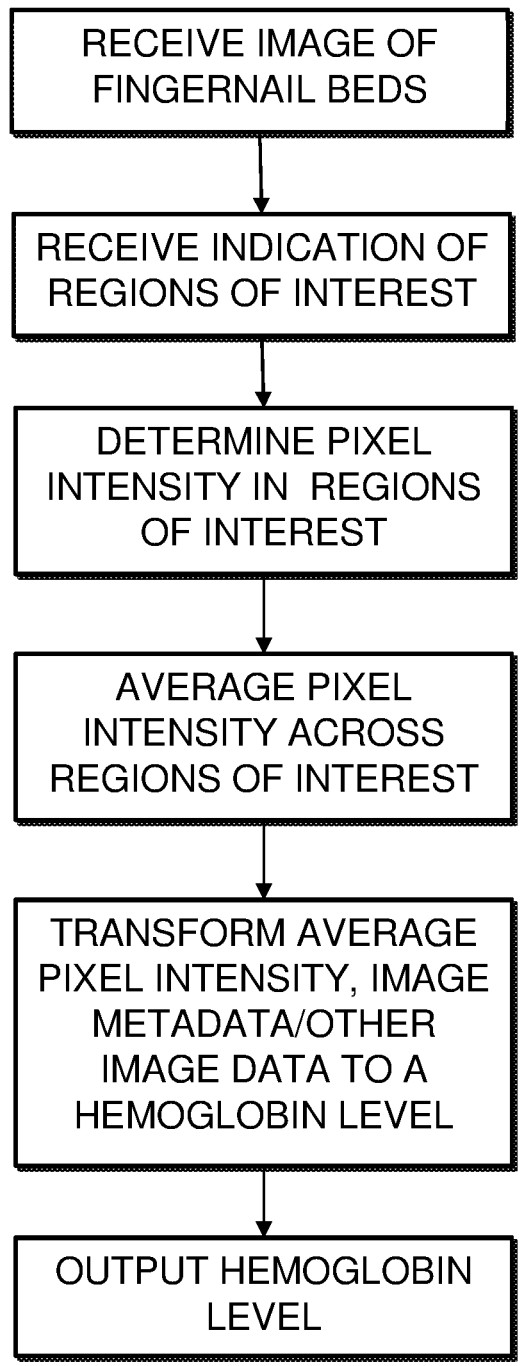
FIG. 1 is a flowchart of a method to determine the user's approximate hemoglobin (Hgb) level from an image of the user's fingernail beds suitable for implementing the several embodiments of the disclosure.

It should be understood at the outset that although illustrative implementations of one or more embodiments are illustrated below, the disclosed systems and methods may be implemented using any number of techniques, whether currently known or in existence. The disclosure should in no way be limited to the illustrative implementations, drawings, and techniques illustrated below, but may be modified within the scope of the appended claims along with their full scope of equivalents. Use of the phrase "and/or" indicates that any one or any combination of a list of options can be used. For example, "A, B, and/or C" means "A", or "B", or "C", or "A and B", or "A and C", or "B and C", or "A and B and C".

A new paradigm of completely non-invasive, on-demand diagnostics is introduced that may replace common blood-based laboratory tests requiring only patient-sourced smartphone photos. The smartphone app disclosed herein estimates hemoglobin levels by analyzing photos of fingernail beds and the metadata that is associated with each image for color and light calibration thereby requiring only the native hardware of the smartphone itself without the need for any external equipment. The app detects anemia (hemoglobin levels <12.5 g/dL) with an accuracy of ±2.4 g/dL and a sensitivity of 97% (95% CI, 89%-100%) when compared with CBC hemoglobin levels (n=100 subjects), indicating the viability for this test to serve as a noninvasive anemia screening tool. Moreover, with personalized calibration, an accuracy of ±0.92 g/dL of CBC hemoglobin levels (n=16) was achieved, empowering chronic anemia patients to serially monitor their hemoglobin levels instantaneously and remotely. The on-demand system enables anyone with a smartphone to download an app and immediately detect anemia anywhere and anytime. Moreover, the approach is broadly applicable to other blood-based biomarkers, has significant potential to reduce healthcare costs, and is well-suited to global health applications.

Here, the observation that pallor is associated with anemia is leveraged to develop a method that quantitatively analyzes pallor in patient-sourced photos using image analysis algorithms to enable a noninvasive, accurate quantitative smartphone app for detecting anemia. At the same time, quality control software is implemented to minimize the impact of common fingernail irregularities (e.g. leukonychia and camera flash reflection) on Hgb level measurement. For example, color values outside of an expected color range may be filtered from the patient-sourced photos. To validate the method, a clinical assessment of this smartphone-based technology using blood samples and smartphone fingernail images of patients with anemia of different etiologies as well as healthy subjects was conducted.

With this technology, a user downloads an app onto their smartphone, takes a photo of his/her fingernail beds, and instantaneously receives an accurate Hgb level which is displayed directly onto the smartphone screen by the app. Since fingernails, conjunctiva, and palmar creases do not contain melanocytes (melanin producing skin cells), the primary source of color of these anatomical features is blood Hgb 18. Of these sites, fingernails are straightforward for a user to self-image, unlike conjunctiva, and also have low person-to-person size and shape variability, unlike palmar creases.

The approach represents a substantial conceptual advance over all other published POC anemia detection tools, since prior techniques require external equipment, such as calibration cards, background light blocking devices, smartphone attachments, or expensive spectrometry readers. Here, a fully functional and standalone smartphone app that enables the non-invasive measurement of blood Hgb levels has been developed and has several advantages over existing approaches. The app technology leverages the image metadata, a vast trove of information that has been completely ignored by every published study to date that uses smartphones for diagnostics. By mining this rich source of information as well as the color data with a robust multi-linear regression approach, the app is the first and only system to date in which accurate Hgb measurements are obtained with a smartphone without the need for any external equipment. Indeed, while smartphone images automatically record metadata, instead of examining this data, other groups have used physical strategies such as color calibration cards and light blocking enclosures. By eliminating external equipment, this system enables "on demand" Hgb level measurement as it requires only the user's smartphone and can be conducted in under 1 minute. Therefore, users who desire to screen themselves for anemia can do so immediately by just downloading an app without being required to wait for external equipment to be shipped to their homes, which even other smartphone anemia tools require. Furthermore, this smartphone-based technique will empower patients to take control of their clinical care via self-testing of Hgb levels.

Anemia screening using the smartphone app.

Figure 3A:
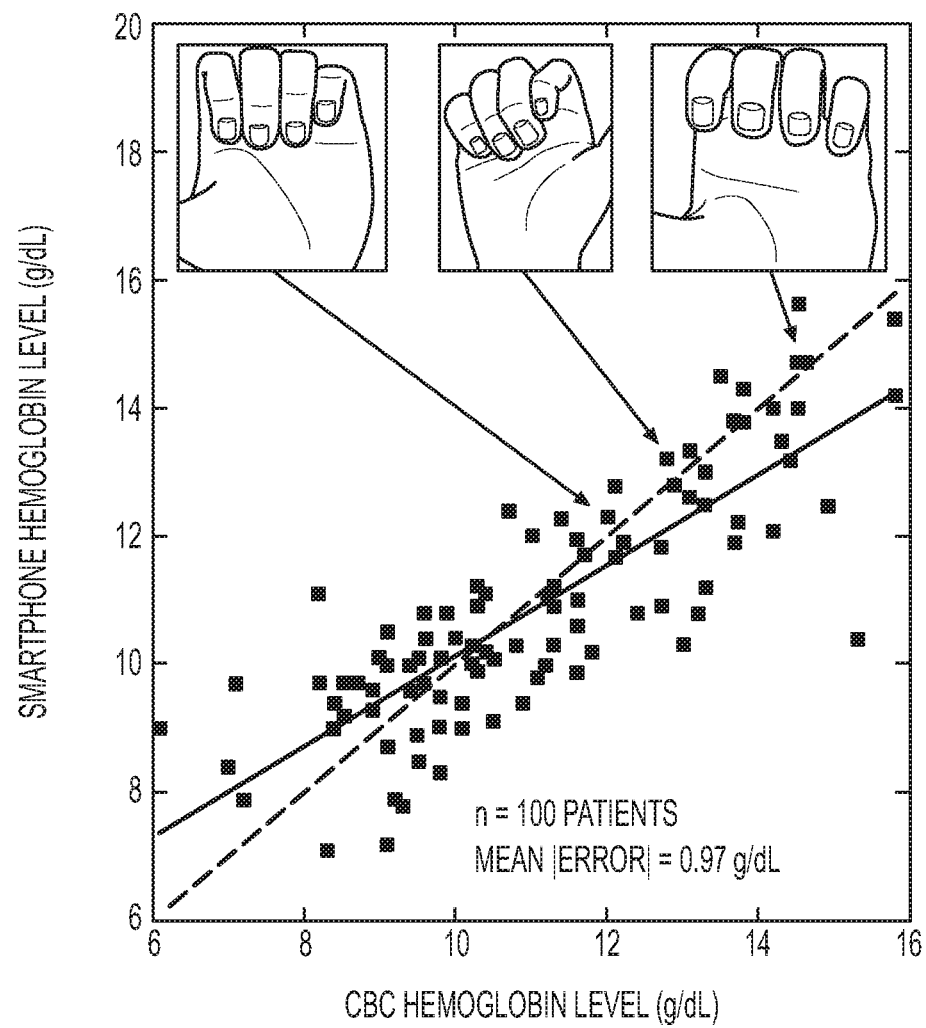
FIGS. 3A-3C illustrate measures of the accuracy of the hemoglobin image analysis algorithm.
Figure 3B:
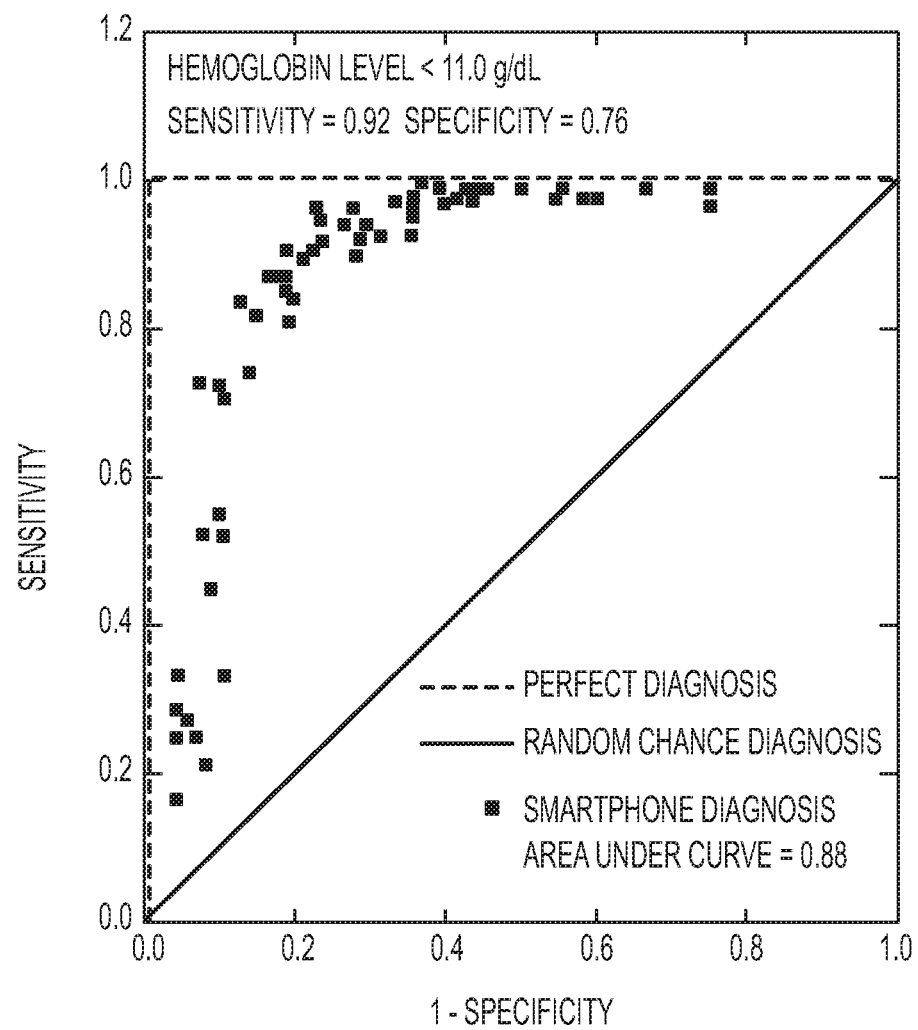
Figure 4:
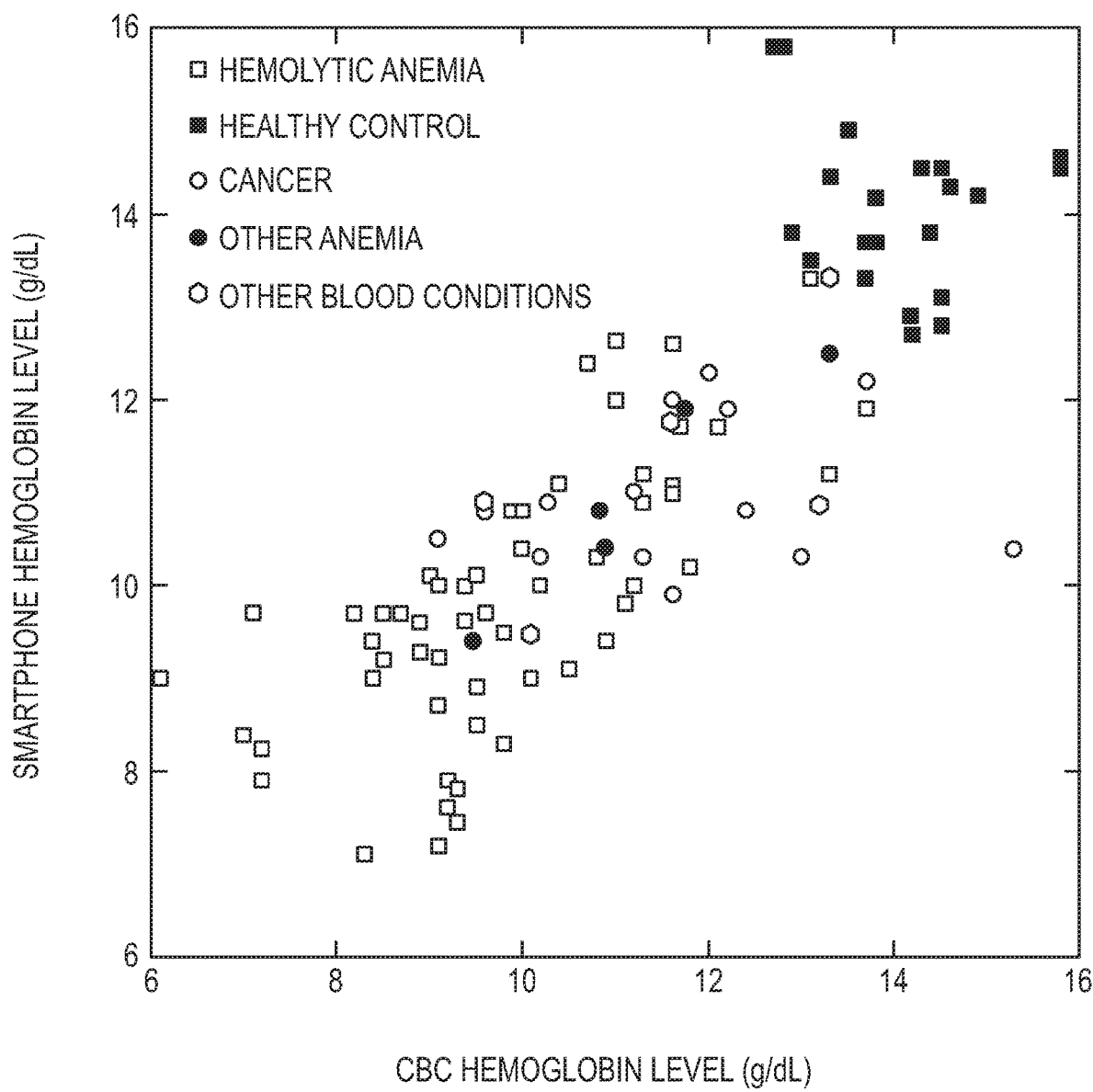
FIG. 4 illustrates a diagnosis profile of the hemoglobin measurement.

This system has the capacity to serve as a noninvasive anemia self-screening tool for use by the general population or at risk populations. With a single smartphone image and no personalized calibration step, smartphone Hgb levels were measured to within ±2.4 g/dL with a bias of 0.2 g/dL of CBC Hgb levels in 100 patients with a variety of anemia diagnoses mixed with healthy subjects (FIG. 3A, r=0.82; FIG. 4), defined as the 95% limits of agreement (LoA). This noninvasive approach represents a greater degree of accuracy than reported accuracy levels of existing invasive POC anemia screening methods. Moreover, receiver operating characteristic analysis revealed that this test achieves a strong diagnostic performance with an area under the curve of 0.88 (FIG. 3B) and highlights the accuracy of this technology throughout the entire range of tested Hgb levels. Additionally, there was minimal correlation between patient Hgb levels and smartphone-measured residual (r=0.26), indicating that the algorithm performance remained consistent throughout range of tested Hgb levels (FIG. 2C). Notably, when using a cutoff of <11.0 g/dL to define anemia, a well-established Hgb level threshold (FIG. 3B), the sensitivity and specificity of the system to detect anemia was 92% (95% CI, 80%-97%) and 76% (95% CI, 62%-87%), respectively. Using the average WHO Hgb level cutoff for anemia of 12.5 g/dL in men and women, the sensitivity of the test improves to 97% (95% CI, 89%-100%), indicating the potential for this test to serve as a noninvasive screening tool for anemia. In fact, this degree of accuracy is on par with reported accuracy values in POC settings of the invasive clinically used Hemocue and substantially better than underdevelopment POC screening tools such as HemaApp and conjunctival analysis via photographs.

Personalized Hgb level measurements using the smartphone image-based algorithm.

Figure 9:
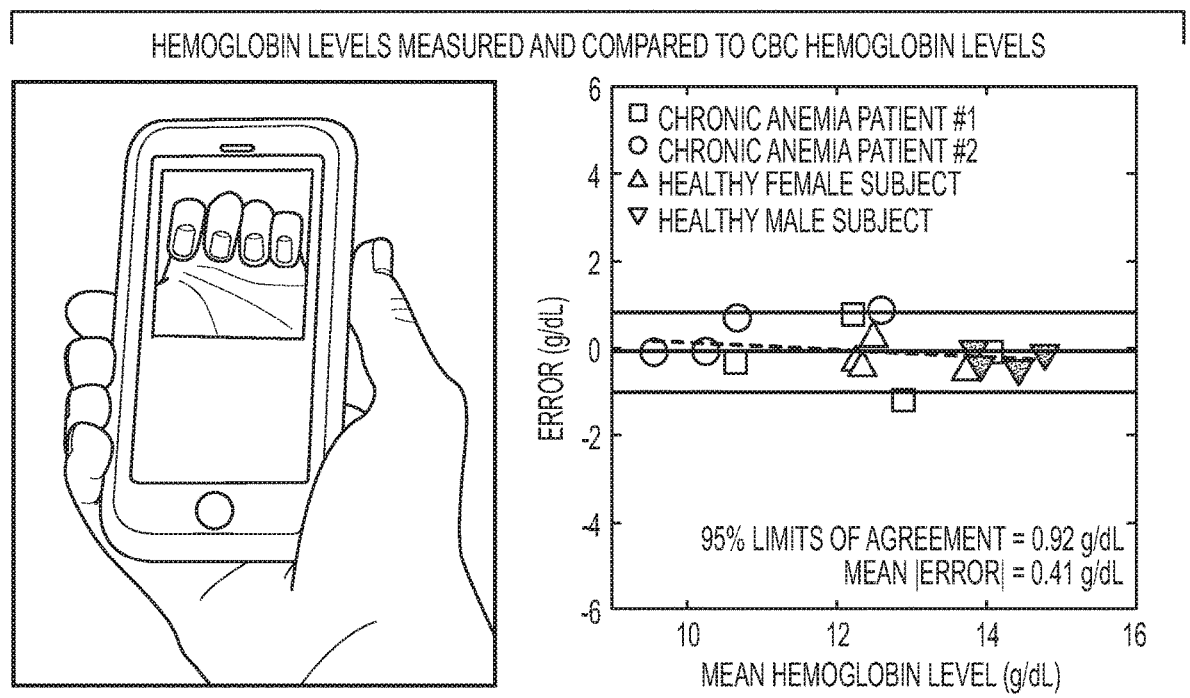
FIG. 9 illustrates an improvement in accuracy in measured hemoglobin levels by adding a personalized calibration to the hemoglobin image analysis algorithm.

Although the accuracy is excellent for a screening tool, individual calibration of the algorithm eliminates some of the measurement error introduced by subject-to-subject variability and therefore further improves the accuracy. Thus, the smartphone-based algorithm was calibrated for each subject. Overall, when used in this manner, this system achieved a level of accuracy of ±0.92 g/dL with a bias of 0.09 g/dL compared to CBC Hgb levels, again, defined by the 95% LOA (i.e. the Hgb level difference from the gold standard that 95% of smartphone measurements will fall between), representing an improvement on the reported accuracy of current invasive, point-of-care hemoglobin tests, such as Hemocue 9, and clinically-used noninvasive methods such as the Masimo Radical. The standard deviation used to calculate the 95% LOA in this case was determined via a random effects model, which takes intrapatient variance caused by repeated Hgb measurements of each patient into account. This indicates that Hgb level measurement error is consistently low across a small, yet diverse study sample size (2 subjects suffering from chronic anemia, 1 healthy male subject, and 1 health female subject). Additionally, the smartphone Hgb level measurement residual did not correlate with the average between each patient's CBC Hgb level and smartphone Hgb level with (r=−0.24), indicating that residuals were not biased for any specific range of Hgb levels (i.e. algorithm performance remained fairly constant throughout the entire physiologic range of tested Hgb levels) (FIG. 9). Furthermore, this degree of accuracy falls below a clinically significant threshold for Hgb level measurement of ±1 g/dL, suggesting that this system can potentially be considered interchangeable with the CBC Hgb level given further study and an increased sample size. Furthermore, 93% of measurements fall within Clinical Laboratory Improvement Amendment (CLIA) allowable total error of ±7%, indicating that, upon further refinement and completion of additional testing, this technology may potentially be viable for at-home and clinical use for diagnosis of anemia in addition to the screening capability of the app when uncalibrated.

Figure 10A:
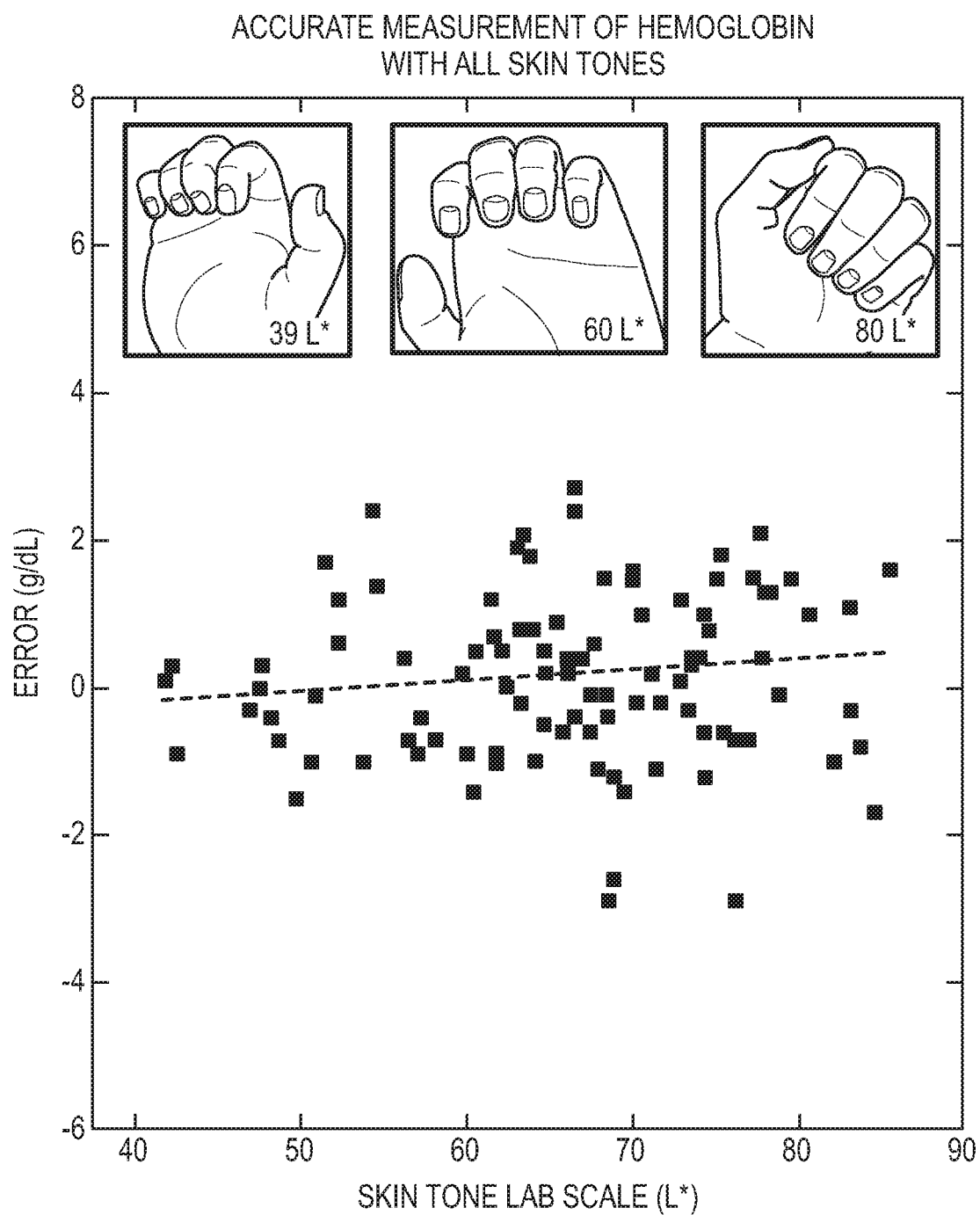
FIGS. 10A-10B illustrate the effect of skin tone and background lighting on the error in measured hemoglobin levels.

The smartphone anemia app is agnostic to potential sources of interference and variability, including skin tone and background lighting conditions. Use of fingernail beds as the imaging area is ideal due to the fact that fingernail beds contain minimal amounts of melanin compared to other parts of the skin, enabling this technique insensitive to subject skin tone. To address this experimentally, images were converted into the CIELab color space, a commonly used color quantification system that quantifies color as perceived by the human eye. In particular, the L* value in this color space has been shown to serve as a linear indicator of skin tone. The relationship between the subjects' skin tones and Hgb measurement residuals was determined by measuring the L* value of a patch of skin adjacent to the fingernail. L* did not correlate (r=0.13) with Hgb measurement residual, indicating that subject skin tone has little impact on the ability of the smartphone system to measure Hgb levels (FIG. 10A).

Figure 10B:
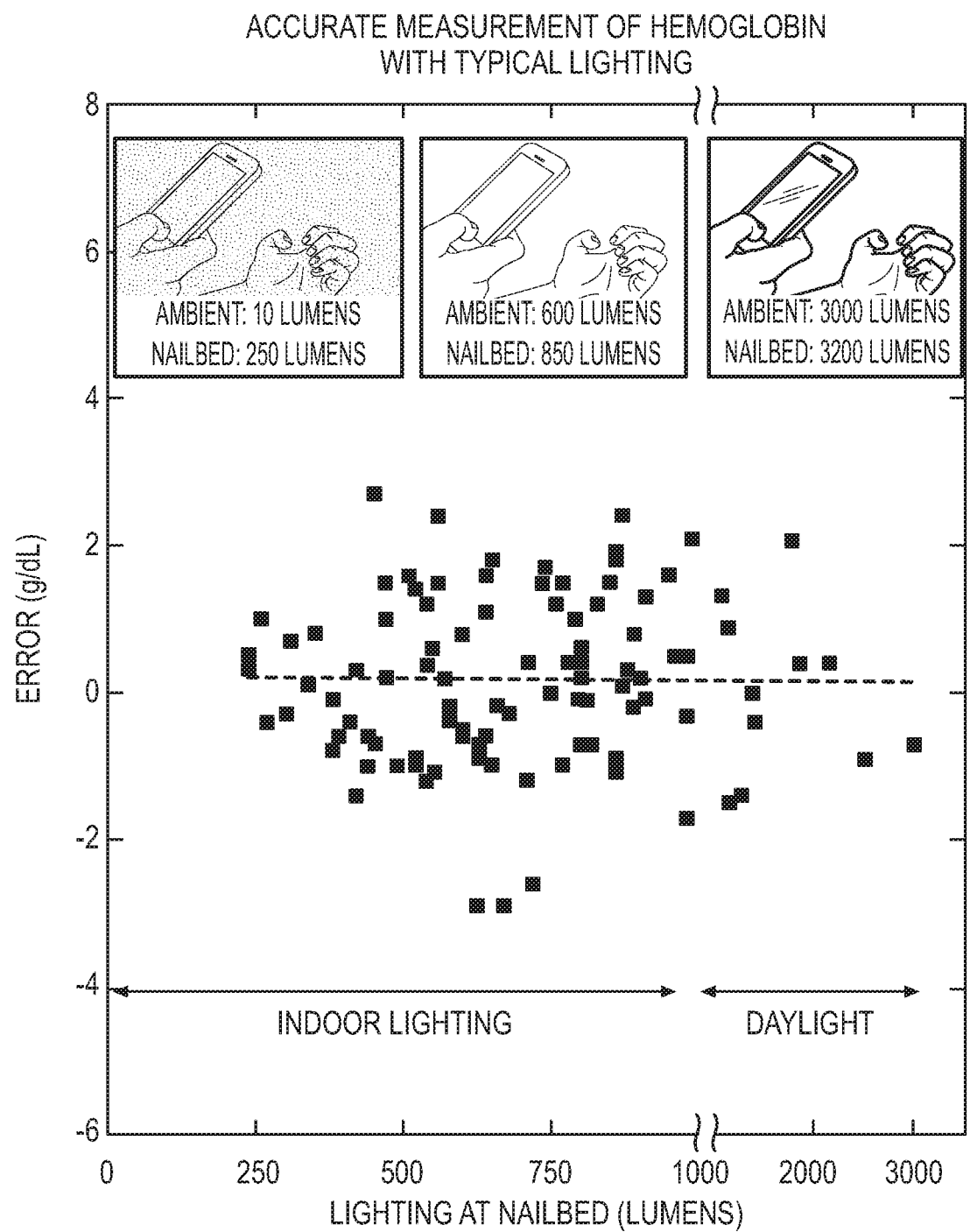

For accessibility in dynamic clinical settings, the smartphone app must function under a wide variety of background lighting conditions. To that end, using luminous flux readings on a digital light meter, no correlation (r=0.00) was found between room brightness and Hgb measurement residual, indicating that this method can be used in a wide variety of settings and lighting conditions (FIG. 10B). Use of the camera flash resulted in the most accurate Hgb level measurement, likely due to the normalization of background lighting conditions provided by the camera flash (FIGS. 6A-6D). Furthermore, ensuring that the technology is agnostic to the smartphone make and model, RGB pixel intensity values of the subject's fingernail beds and a control patch of skin were found to be similar between images taken with smartphones made from different manufacturers and models (FIG. 7A). Additionally, no statistically significant difference existed between pixel intensity values of fingernail bed images obtained by two different smartphone (FIG. 7B). Finally, the precision of Hgb level measurements using our technology was found to be ±0.17 g/dL when tested on multiple images of the same individual's fingernails. Furthermore, preliminary studies suggest that hand temperature and exercise status do not impact Hgb level measurement, indicating that the app may be agnostic to fingernail perfusion variability.

Figure 11A:
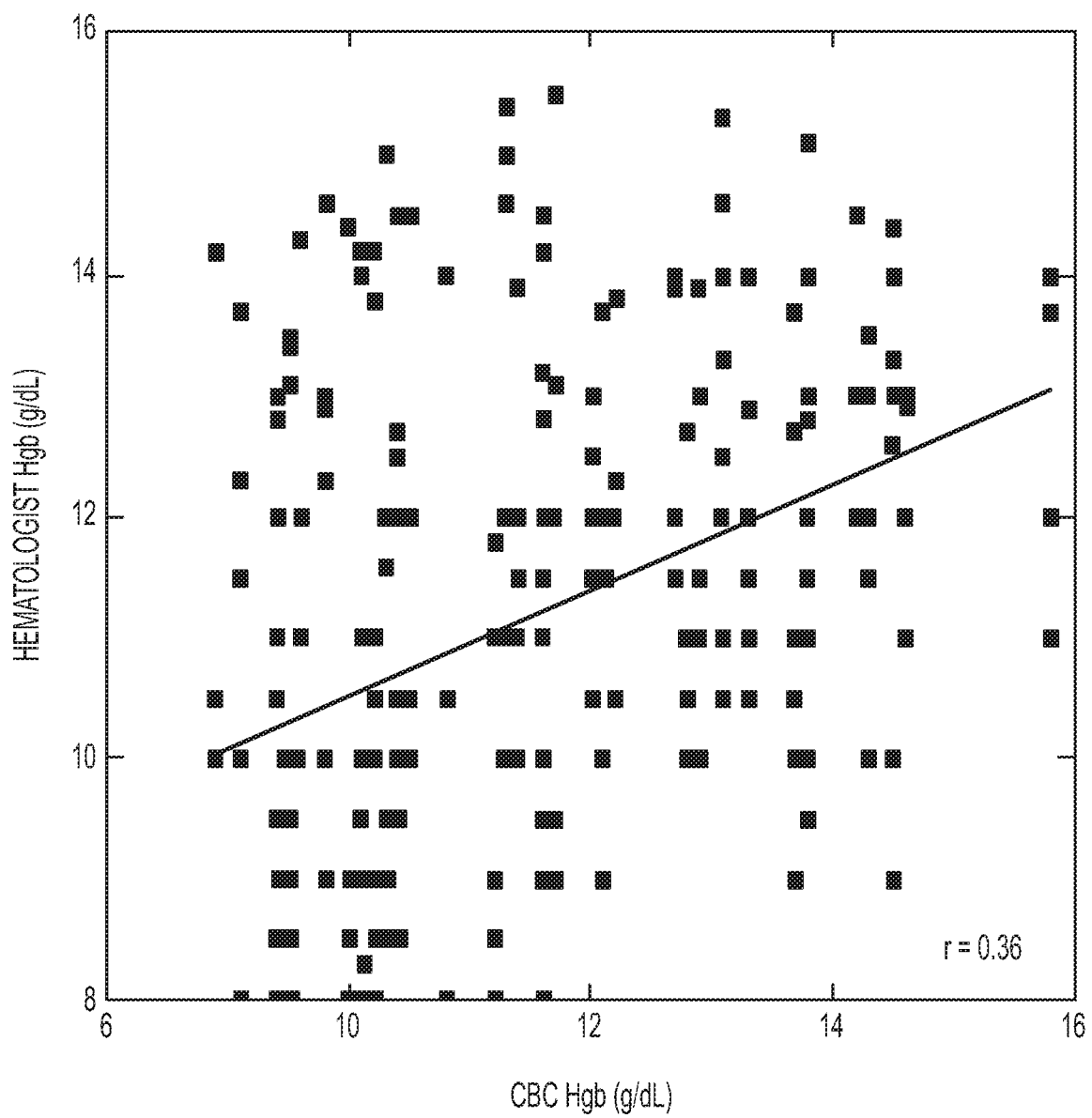
FIGS. 11A-D illustrate comparisons of accuracy of hemoglobin measurements by hematologists as compared to the hemoglobin image analysis algorithm.
Figure 11B:
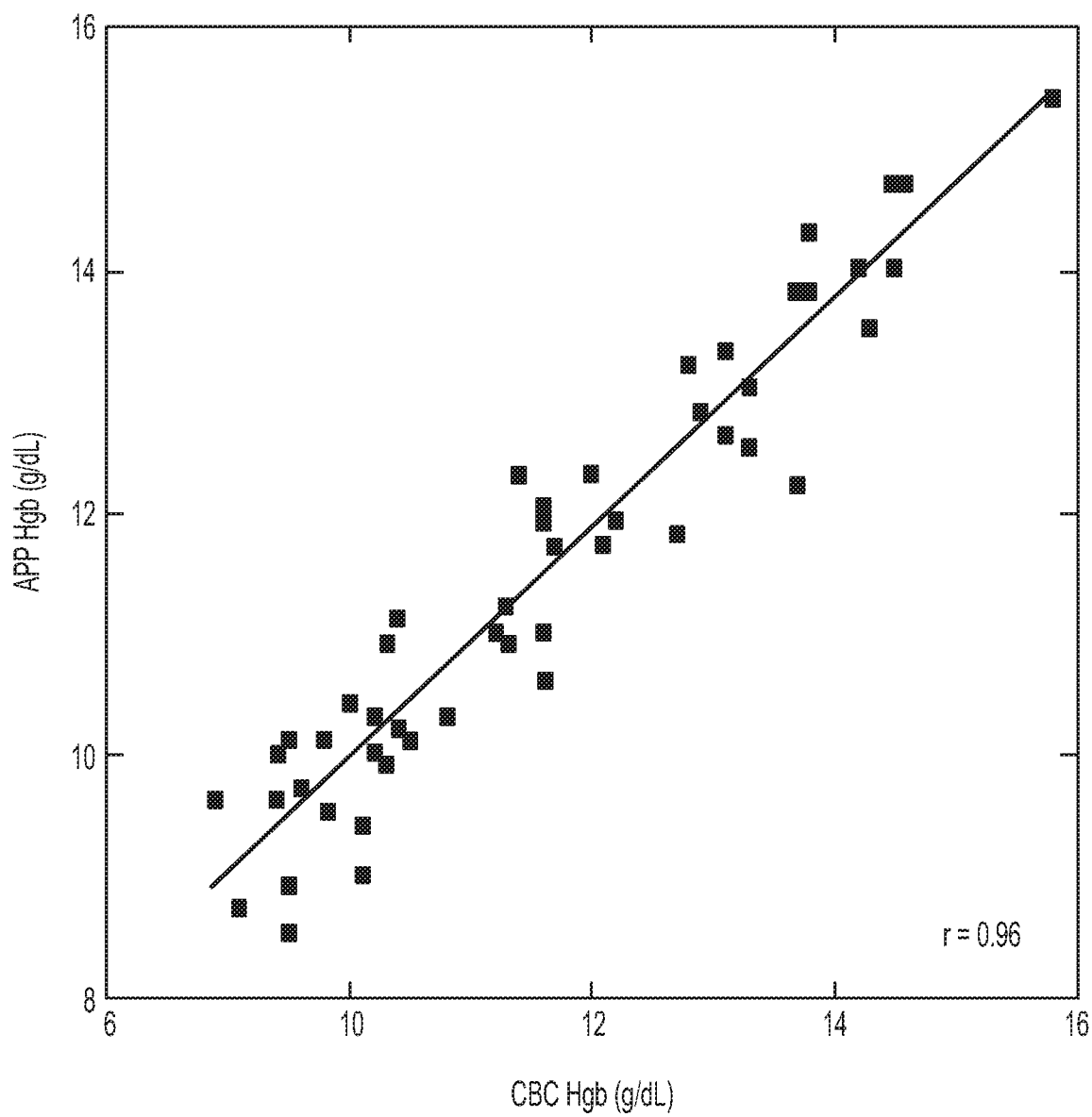

The app outperforms clinical hematologists' ability to measure Hgb levels via physical examination. Clinical hematologists, US Board certified physicians who specialize in the clinical care of patient with blood disorders, were asked to measure Hgb levels in patients via inspection of images of fingernails. In order to account for physician bias associated with physical examination of patients (e.g. prior knowledge of the patient's medical history), the physicians reviewed the same images of the patients' fingernails as the app. This approach better compares the diagnostic capabilities of physicians and the app. When estimating Hgb levels based on examinations of images of patient fingernail beds (n=50), hematologists estimated blood Hgb levels to within ±4.6 g/dL of the CBC Hgb level (FIG. 11A). Note that this degree of accuracy represents nearly the entire physiologic Hgb level range tested. The app was then tested on the dataset of 50 patient images and measured Hgb to within ±1.0 g/dL of CBC Hgb levels (FIG. 11B).

Figure 11C:
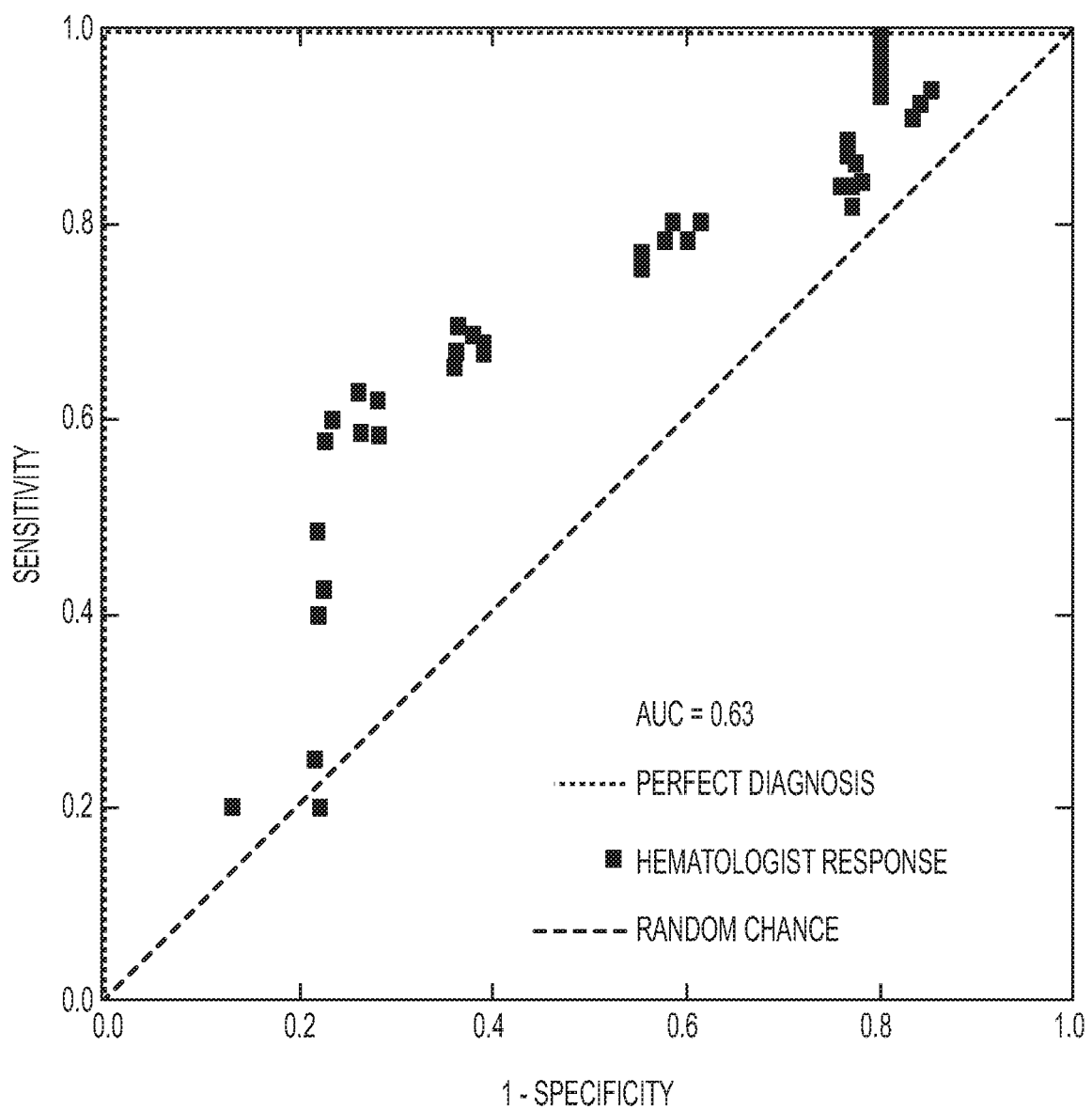
Figure 11D:
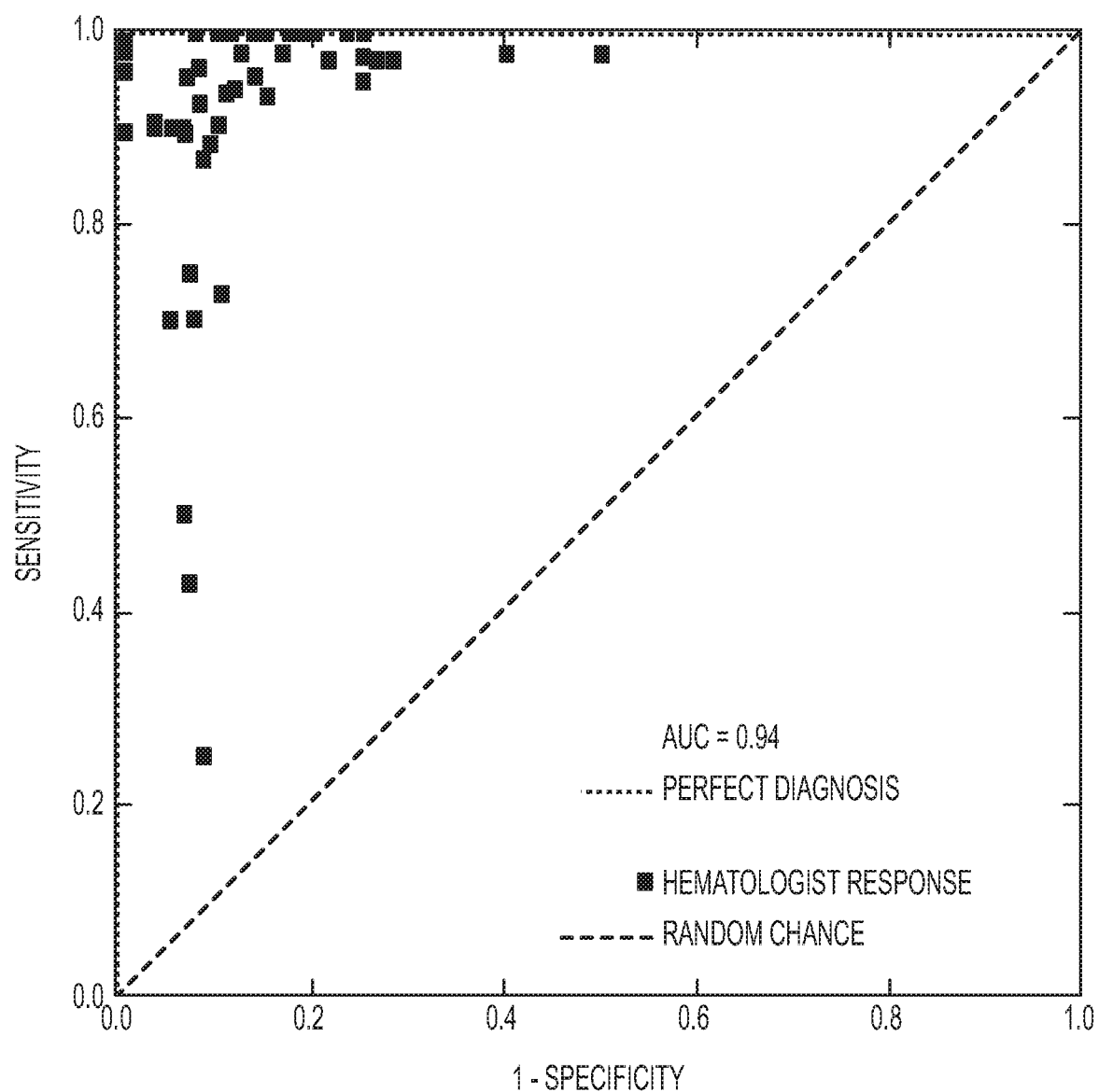

Furthermore, ROC analysis revealed an area under the curve of 0.94 for the app vs 0.63 for the hematologists, representing a significant improvement in diagnostic accuracy (FIGS. 11C-11D). Moreover, agreement of Hgb levels between the physicians' estimates, the smartphone app, and CBC Hgb levels was assessed using the intraclass correlation coefficient (ICC), which found that the smartphone all and CBC Hgb levels demonstrate excellent agreement (defined as ICC <0.9) as ICC is estimated to be 0.95 (95% confidence interval (CI): 0.92-0.97), while an average of the 5 hematologists' evaluations demonstrated only moderate agreement with the CBC Hgb levels, with an ICC of 0.59 (0.37-0.74). Importantly, inter-physician variability of Hgb level estimates were high, as indicated by the low level of agreement with an ICC of 0.20 (95% CI 0.07-0.36).

Discussion:

Given the performance of this technology and high prevalence of anemia worldwide, afflicting nearly two billion people, especially young children, the elderly, and pregnant women, worldwide, this completely noninvasive technology that requires only photos obtained from smartphones has significant implications as a widely accessible screening tool for at risk populations and the general population. The ability to inexpensively diagnose anemia with a high sensitivity, completely noninvasively and without the need for any external smartphone attachments or calibration equipment represents a significant improvement over current POC anemia screening. The external equipment requirements of current existing POC anemia screening technologies represent a significant hurdle for use, as each additional piece of equipment requires a supply chain to support it. For example, even relatively low-cost color calibration cards used to normalize for different background lighting require distribution to the patient and quality control measures regarding the manufacturing process to ensure that the colors are printed precisely and accurately on each card.

In addition, while our system can be used for both anemia screening and diagnosis, it is important to contextualize the accuracy requirements of these different clinical scenarios. Though clinical diagnostic tools for anemia have strict accuracy requirements (±1.0 g/dL), these requirements are less stringent in POC settings, where anemia screening, rather than diagnosis is crucial. Our results indicate that this smartphone app is ideally suited for screening anemia. Indeed, the accuracy we have presented (±2.4 g/dL) is comparable or better than currently available POC diagnostic tools such as the invasive Hemocue (±2.3 g/dL), the expensive Masimo (±3.7 g/dL), and the invasive WHO Color Scale (±3.3 g/dL). Furthermore, the results of the app when individually calibrated suggest that this technology achieves Hgb measurement accuracy necessary for anemia diagnosis.

Optimizing sensitivity is of paramount importance for a screening tool, due to the ability to correctly identify a high percentage of anemia cases even if this negatively impacts specificity. In its current form, the app requires the user to simply obtain a fingernail image, which can then be analyzed with an on-board smartphone app that comprises an image analysis algorithm to output the Hgb level measurement or be transmitted remotely to another device (e.g. laptop, desktop computer, cloud-based server with the algorithm embedded into their systems) for remote analysis, the results of which can be immediately transmitted back to the user. After identifying subjects that may possibly be anemic, either type of system can recommend confirmatory Hgb level testing with a CBC, allowing any false positives to avoid unnecessary treatment. Given the ever-increasing rate and near ubiquity of smartphone ownership worldwide, this noninvasive, inexpensive, patient-operated Hgb measurement algorithm allows those at risk of anemia to monitor their conditions using only the native hardware included with their own smartphone.

Additionally, this system has the potential to fundamentally alter the management of patients with chronic anemia. During the course of several weeks, a patient may take images of their fingernail beds and enter their CBC-measured Hgb levels that were obtained as part of their regular outpatient clinical care. Results suggest that these images and Hgb levels may be used to "teach" the smartphone phone to develop a "calibration" personalized and tailored to each individual patient. In times of clinical stress, these patients, such as those with genetic causes of anemia or cancer undergoing chemotherapy, may experience rapid, life-threatening, precipitous drops in Hgb and require constant monitoring to determine their need for transfusions. Using this technology, patients could potentially self-monitor their anemia from the comfort of their own home, rather than through inconvenient and recurring clinic visits. In addition, some patients with chronic anemia due to a genetic etiology require chronic transfusions to survive. These scheduled transfusions are currently administered at convenient and regular intervals, and not based on clinical need. Hence, a patient may be transfused too early, exposing them to unnecessary transfusion-related effects (i.e. iron overload, risk of infection), while patients transfused too late may require urgent hospitalization if they develop symptomatic anemia or their Hgb levels decrease to a dangerous level. By enabling continuous and simple monitoring, this technique may empower patients and lead to better allocation of blood bank resources.

Moreover, further data collection will increase the size of the patient image pool, facilitating the incorporation of deep machine learning techniques to further refine the Hgb measurement algorithm. Furthermore, this CBC-validated, smartphone image-based smartphone app for measuring Hgb has the potential to dramatically improve upon the accuracy, cost, and convenience of current Hgb measurement devices while also eliminating the need for anything other than a smartphone, representing a significant improvement over other POC Hgb measurement technologies. With this smartphone image-based Hgb measurement system, any person—healthy or ill—in any location, at any time, now has access to an important health metric and may seek care accordingly. Moreover, healthcare officials in low resource settings may use this technology to inform allocation of limited healthcare resources (e.g. transfusions, high-risk obstetrical services) and medications (e.g. nutritional supplementation such as iron, folate, or vitamin B12) for the patients with the most severe anemia. This completely noninvasive, algorithm-based approach represents a paradigm shift in the way anemia can be screened, diagnosed, and monitored globally. As the system requires no reagents or equipment, the healthcare cost savings could also be significant.

Overall, the ability to conduct self-testing using an unmodified smartphone presents significant advantages over previously reported technologies which require additional equipment such as calibration cards and light-blocking rigs. Moreover, the app utilizes metadata that is automatically obtained from the smartphone camera which enables normalization of background lighting conditions. This presents significant conceptual advantages over existing Hgb measurement technologies, as Hgb levels can now be measured by a patient without requiring a clinic visit or any cumbersome external equipment.

This system suffers from the potential to be impacted by diseases which cause nailbed discolorations such as jaundice and cyanosis. However, it is important to point out that a large population of our study subjects suffered from hemolytic anemias, which can lead to jaundice. No correlation was found between disease state and Hgb measurement error, indicating that jaundice is unlikely to impact Hgb measurement (FIG. 9). Furthermore, the image analysis algorithm can potentially be trained in future studies on populations with these disorders to take these discolorations into account. While these conditions may present challenges in Hgb measurement, they present a promising opportunity to use the app to screen for such diseases.

Overall, the ability to conduct rapid on-demand self-testing demonstrates the versatility of the system and could be especially conducive for global heath applications, where remote diagnosis coupled with tight quality control measures may be preferred and enabled by increasing smartphone use and mobile network prevalence in low resource settings. This approach will shift the anemia screening paradigm worldwide by empowering patients to test themselves from the comfort of their own homes, wherever and whenever they desire.

Methods:
Algorithm Development/Image Processing

In an example, smartphone images are transferred or transmitted from the smartphone to a computer. Fingernail data, skin color data, and image metadata is extracted from fingernail bed smartphone images via image processing software, such as MATLAB (Mathworks, Natick, MA). Regions of interest, from which fingernail and skin color data were extracted, may be manually selected to ensure that fingernail irregularities were excluded from analysis. In some implementations, regions of interest may be automatically selected. For example, a region of interest may be automatically selected for each fingernail upon identification of each fingernail and selecting a region on each fingernail that minimizes a number of pixels filtered based on the filtering criteria discussed below. Other techniques may be used to automatically select regions of interest.

Figure 8:
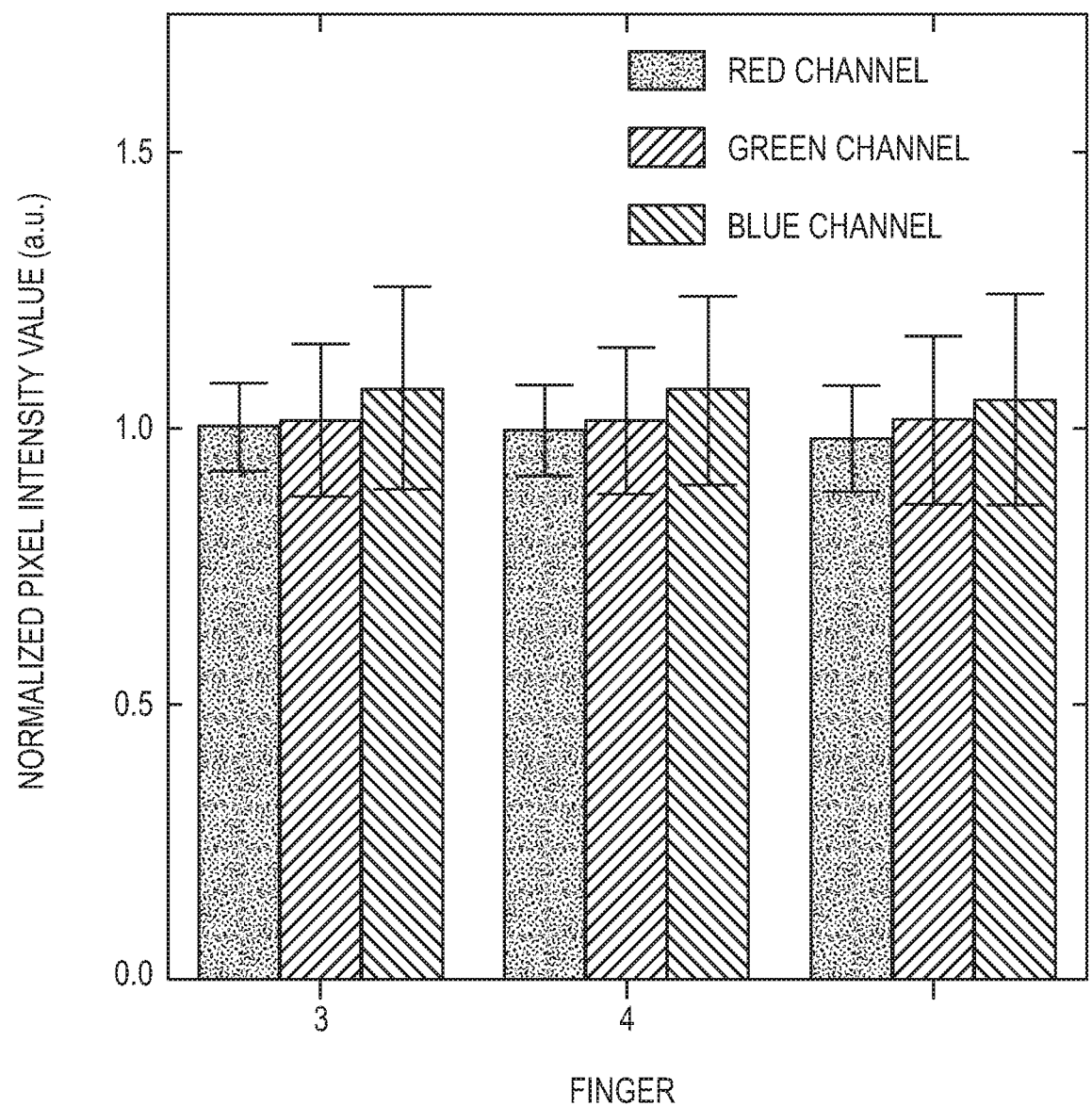
FIG. 8 illustrates the variability of color values of different fingernails on the same individual.

The regions of interest are selected from each finger, excluding the thumb. In an example, each of the regions of interest is 900 pixels, corresponding to approximately 10 mm$^2$ on each fingernail. The number of pixels may vary depending on the resolution of the image sensor capturing the image. Color data is extracted from each region and averaged together across fingers for each subject. Averaging the color data is acceptable due to the low color variability between different fingers (FIG. 8). A Hgb determination algorithm uses robust multi-linear regression with a bisquare weighting algorithm to relate the image parameter data to manually measured CBC Hgb levels.

$$\text{HemoglobinResult} = C + P1*W1 + P2*W2 + \ldots Pn*Wn \quad \text{Equation 1:}$$

Where: C=constant, W=weights determined via robust multi linear regression, and P=skin color data, fingernail color data, and image metadata parameters.

A uniform bias adjustment factor may also added to address the inherent variability in fingernail measurement. Two distinct use models and algorithms may be used for this Hgb measurement method: 1) as a noninvasive, smartphone-based, quantitative Hgb level diagnostic requiring calibration with patient-specific CBC Hgb levels that enables chronic anemia patients to self-monitor their Hgb levels, and 2) as a noninvasive, smartphone-based anemia screening test that does not require calibration with CBC Hgb levels.

Anemia Screening Among the General Population

Figure 3C:
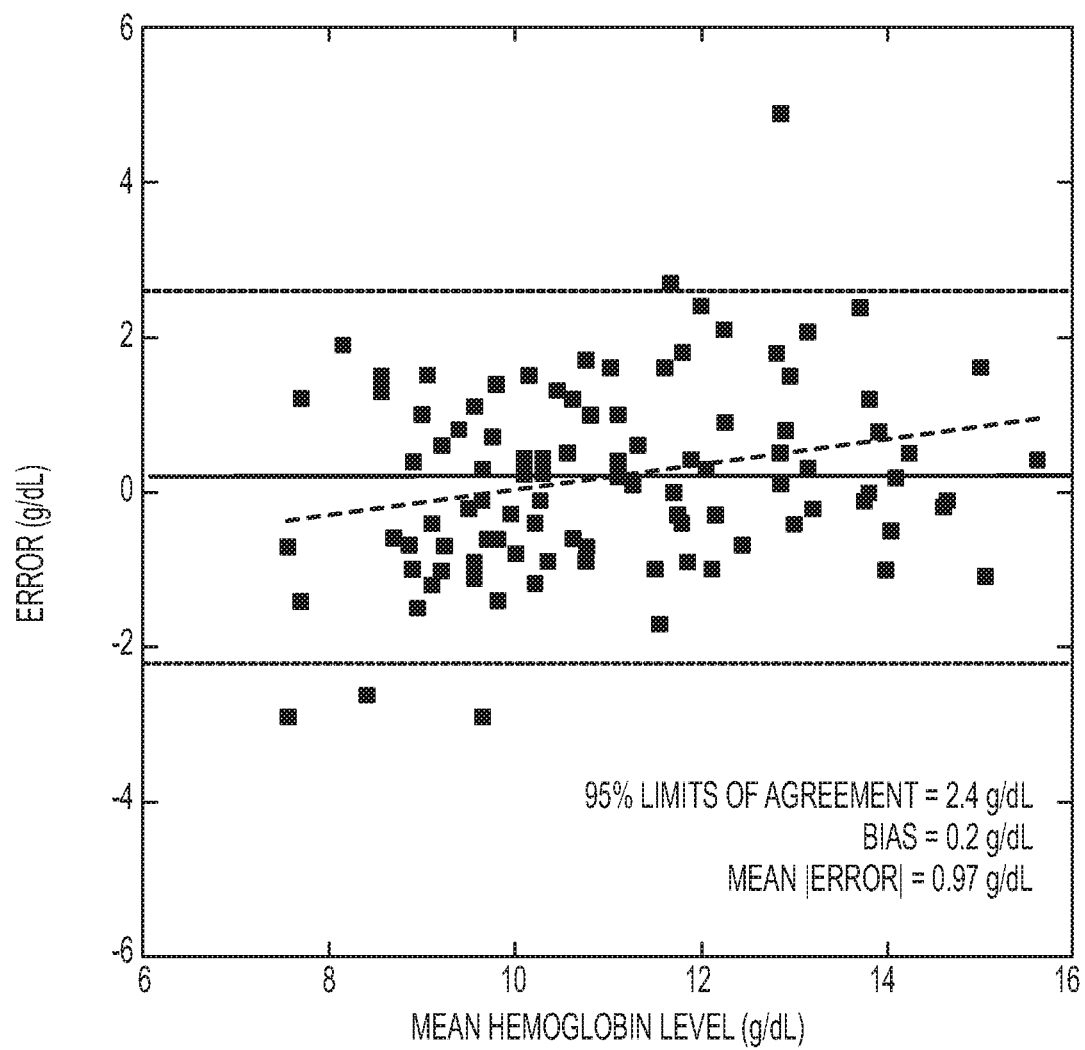

In an example, in development of the screening algorithm to screen for anemia, an entire study population (337 subjects) is randomly split into a "discovery" group (237 subjects) and a "testing" group (100 subjects). The discovery group is used to establish the relationship between image parameters and Hgb levels via robust multi-linear regression, much like the calibration phase of the personalized calibration study. The testing group, analogous to the testing phase of the personalized calibration study, of 100 subjects was used to validate the resultant algorithm. Validation was performed by applying the smartphone algorithm to each testing image and comparing the algorithm generated Hgb result with the CBC Hgb result (i.e. determining the residual of the algorithm-based method). This process was repeated 1000 times with different, randomly-selected without replacement, discovery/testing groups to minimize residual error, thereby optimizing the parameters of the algorithm for anemia screening. Resulting data from most accurate outcome of this optimized screening algorithm is depicted in FIGS. 3A-3C.

Personalized Calibration of Smartphone Processing System

In an example, a personalized calibration approach was tested in two β-thalassemia major patients with chronic anemia currently undergoing chronic transfusion therapy, a healthy female subject with Hgb levels that fluctuated during her menstrual cycle, and a healthy male subject with consistent Hgb levels over an identical timeframe to assess the algorithm's capability to be accurately personalized and calibrated to that individual, regardless of their diagnosis or Hgb levels. Treatment for β-thalassemia major currently comprises red blood cell transfusions to compensate for the patients' ineffective erythropoiesis. Hgb levels in the chronic anemia patients fall throughout a 4 week transfusion cycle. Smartphone images are obtained with and without the camera flash. Prior to each imaging session, CBC Hgb levels are obtained from each subject via venipuncture. Color data and phone metadata are compiled and a relationship between image data and CBC Hgb levels is established via robust multi-linear regression. This process was repeated for each individual using data from the 4 weeks of images to create a unique calibration curve personalized for that individual. Image parameter changes associated with Hgb level fluctuations specific to each person are related to perform algorithm calibration specific to each subject, thus improving the accuracy of Hgb level estimation. After the smartphone image analysis system is calibrated for each subject, Hgb levels were measured weekly over the next 4 weeks using the newly personalized algorithm.

These calibrated Hgb level measurements were then compared to the CBC Hgb levels obtained at the same time to assess accuracy. The personalized calibration occurred over a total of 8 weeks. Hemoglobin measurement from images of fingernails Images are taken of 50 subjects' fingernails from the previously described clinical study. These subjects' ages ranged from 1 to 62 years old. Hematologists (M.D. physicians who specialize in clinical hematology and are trained and Board Certified in the U.S.A.) were instructed to analyze each image and measure Hgb levels. For comparison, images were loaded into the app, and the Hgb measurement protocol was performed on these images. It is important to note that these images were not used in the development of the underlying image analysis algorithm.

Intraclass correlation coefficient (ICC) reflects not only degree of correlation but also agreement between measurements and ranges between 0 and 1, with values closer to 1 representing stronger reliability. Reliability refers to the degree of agreement among raters. It gives a score of how much homogeneity, or consensus, there is in the ratings given by different judges or instruments. The ICC is able to incorporate the reliability of more than 2 raters—as in the case of the 5 hematologists evaluating nail beds. Patients and the physicians were assumed to be random samples from the respective populations they represent.

FIG. 1 is a flowchart of a process for quantitatively analyzing the pallor of a user's fingernail beds to determine the user's approximate hemoglobin level. The process may be executed by a mobile application on a smartphone device or on a remote server or other computer external from the mobile device. As shown in FIG. 1, the process includes receiving an image of one or more fingernail beds of a user from a camera with a flash functionality activated. For example, the mobile application may receive the image from a camera or image sensor on the smartphone device. Alternatively, the server or other computer may receive the image transmitted from the smartphone device along with a request for a determination of a hemoglobin level. An indication of one or more regions of interest on the image are received. The one or more regions of interest at least partially including the one or more fingernail beds. For example, a user of the mobile application may manually specify the regions of interest. In another example, the mobile application may automatically determine the regions of interest. The process continues through a quantitative analysis of the pallor of the one or more fingernail beds in the one or more regions of interest to determine the user's approximate hemoglobin (Hgb) level. Specifically, the process includes determining pixel intensity (e.g., color) for each of the one or more regions of interest.

In some examples, pixel intensity values that fall outside of an expected pixel intensity value range (e.g., color range) are filtered from the region of interest. The process further includes averaging pixel intensity from color channels across each of the one or more regions of interest. The process further includes transforming the average pixel intensity from the color channels into a value that correlates to the user's approximate Hgb level. In addition to the average pixel intensity (e.g., color) of the user's fingernail beds, image metadata/other image data may be used in the transform to the user's approximate Hgb level. For example, image metadata regarding the use of a camera flash or other image capturing parameters (e.g., white balance, focus, etc.) or other image data may be used in the multi-linear regression discussed above.

Figure 2A:
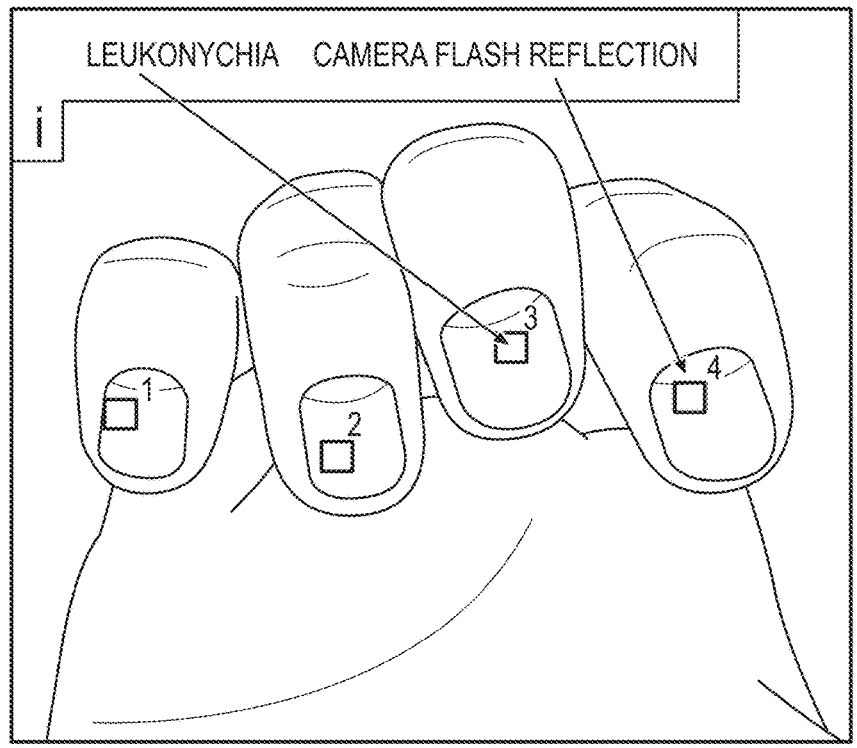
FIGS. 2A-2B illustrates an image of the user's fingernail beds with fingernail irregularities and a quality control process to exclude pixel values corresponding to the fingernail bed irregularities.
Figure 2B:
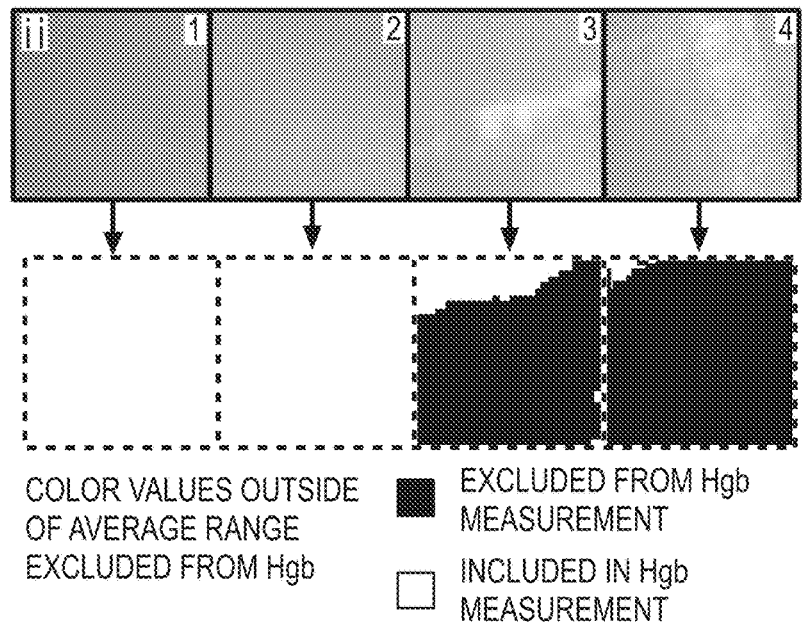

FIGS. 2A-2B illustrates an image of the user's fingernail beds with fingernail irregularities and a quality control process to exclude pixel values corresponding to the fingernail bed irregularities.

Implementation of a smartphone image analysis system into a smartphone app enables noninvasive, patient-operated measurement of blood hemoglobin (Hgb) levels and anemia detection using only patient-sourced photos and the native hardware of the smartphone itself. A patient may simply downloads the app onto their smartphone, open the app, obtain a smartphone photo of his/her fingernail beds, and without the need for any blood sampling or additional smartphone attachments or external calibration tools, quantitatively measures blood Hgb levels. The patient first takes an image of their fingernails, and is then prompted by the app to tap on the screen to select the regions of interest corresponding to the nailbeds, and a result is then displayed on the smartphone screen. As shown in FIG. 2A, smartphone images with fingernail irregularities such as camera flash reflections or leukonychia may affect Hgb level measurements. Therefore, a quality control algorithm integrated within the Hgb level measurement app detects and omits those irregularities to preserve measurement integrity and accuracy. As shown in FIG. 2B, to that end, the user selects regions of interest from within the fingernail image and any color values that fall outside of expected color ranges are excluded from Hgb measurement. In this example, when the quality control system was implemented to exclude the fingernail bed irregularities, Hgb level was measured to be 14.7 g/dL, comparable to the patient's CBC Hgb level of 15.3 g/dL. Without the quality control algorithm, Hgb level was measured at 12.8 g/dL, indicating that the algorithm resulted in a 76% reduction in error. Note that as the smartphone image-based algorithm is device-agnostic, the analysis of the smartphone images, and therefore the Hgb level measurements, could also be transmitted to another device (e.g. laptop, cloud-based server) for remote rather than on-board analysis. In an example, the expected color range is calculated as the standard deviation of the average pixel intensity color values within the selected regions of interest for a corpus of test images. In some examples, the corpus of test images are the same images that are used to generate the robust multi-linear regression.

FIG. 3A-C illustrate measures of the accuracy of the image analysis algorithm. The smartphone-based image analysis algorithm accurately measures Hgb levels. As shown in FIG. 3A, the smartphone image analysis algorithm measures blood Hgb levels to within ±0.97 g/dL of the CBC Hgb level (r=0.82). The solid line represents the ideal result where smartphone Hgb level is equal to the CBC Hgb level whereas the dashed line represents the actual data fit. Inset images illustrate example patient-sourced photos that were used to calculate Hgb level measurements. As shown in FIG. 3B, the Receiver Operating Characteristic (ROC) analysis graphically illustrates the algorithm's diagnostic performance against a random chance diagnosis (diagonal line), with an area under the curve of 0.5, and a perfect diagnostic (bold right-angle line), with an area under the curve of 1. In the case of this noninvasive smartphone app Hgb measurement system (black line), the area under the curve of 0.88 suggests viable diagnostic performance of this algorithm. When using the WHO Hgb level cutoff of <12.5 g/dL, the sensitivity of the test is 97% (95% CI, 89%—100%), n=100 patients. As shown in FIG. 3C, Bland-Altman analysis reveals minimal experimental bias with 0.2 g/dL average error, indicating that Hgb measurement is has a very small bias. The dashed line represents the relationship between the residual and the average of Hgb level measurements obtained from the CBC and the algorithm (r=0.26). The solid horizontal lines represent 95% limits of agreement (±2.4 g/dL).

FIG. 4 illustrates a diagnosis profile of the hemoglobin measurement. Subjects with hemolytic anemia, healthy controls, cancer, other anemia (e.g. aplastic anemia), as well as various other blood disorders (e.g. such as thrombocytopenia, deep vein thrombosis, and hemophilia) participated in the study. These data represent the diagnosis profiles of the subjects shown in FIG. 2.

Figure 5:
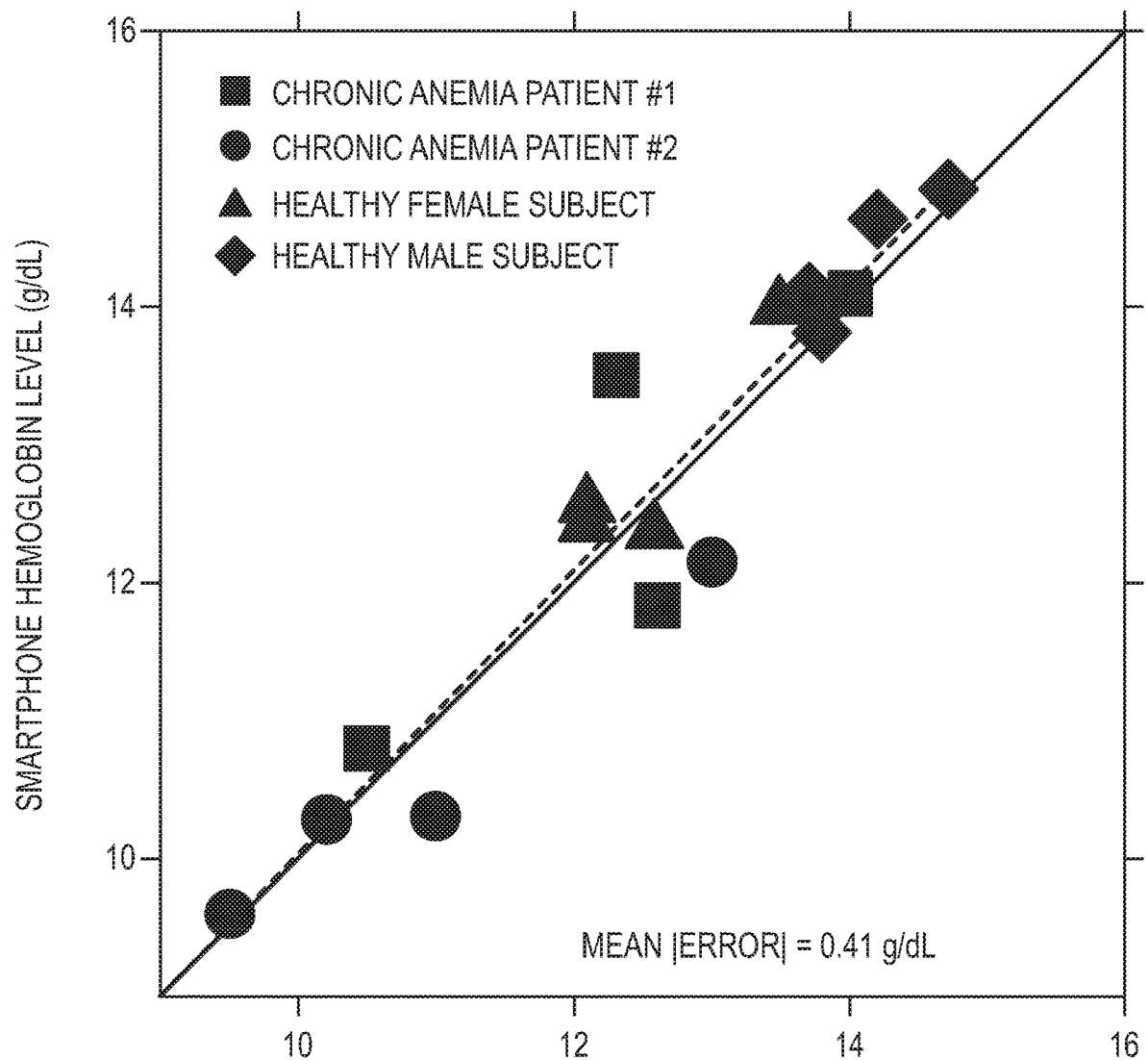
FIG. 5 illustrates a comparison of the image analysis hemoglobin levels to complete blood count (CBC) measurements of hemoglobin levels.

FIG. 5 illustrates a comparison of the image analysis hemoglobin levels to complete blood count (CBC) measurements of hemoglobin levels. Patient-specific Hgb level measurements are in agreement with CBC measurements in the study population throughout a physiologic range of Hgb levels. This patient-specific calibration improved the accuracy of Hgb level measurements to within 0.41 g/dL of the CBC Hgb level (r=0.95). The solid line represents the ideal result where smartphone Hgb level is equal to the CBC Hgb level. The dashed line represents the actual data fit.

Figure 6A:
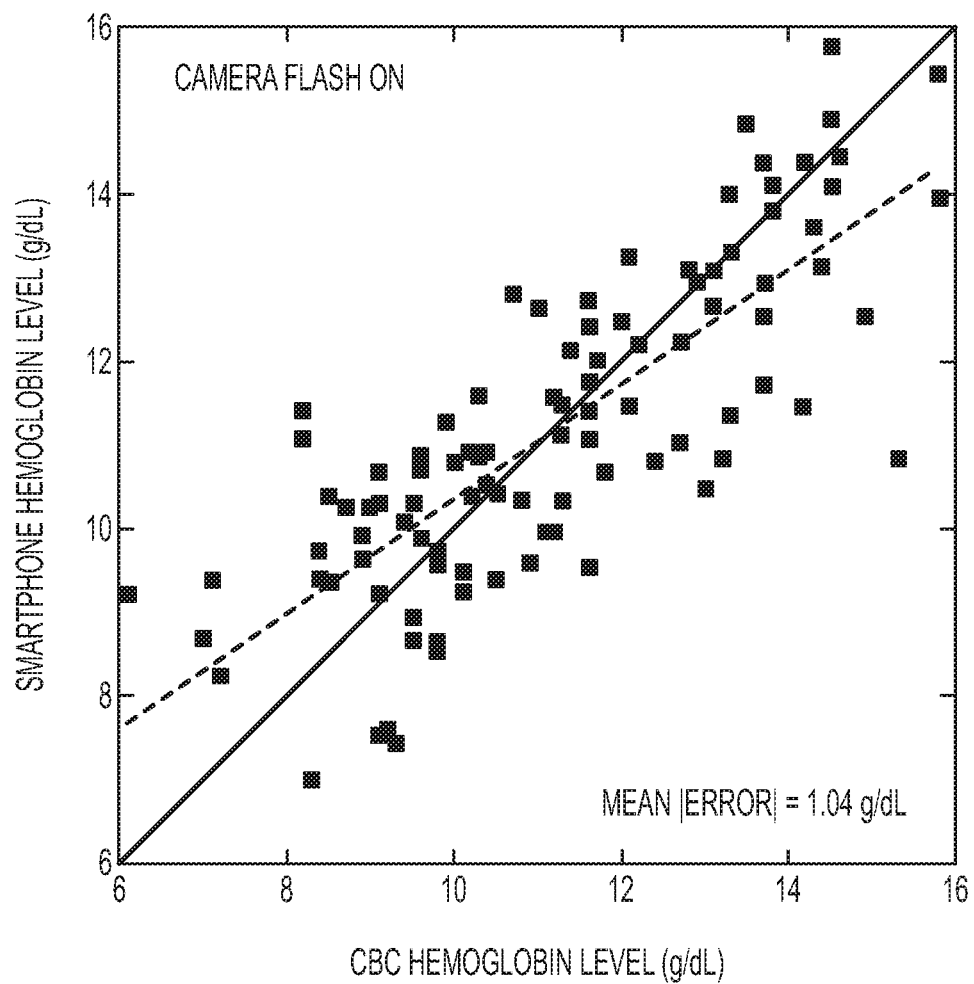
FIGS. 6A-6D illustrate comparisons of the image analysis hemoglobin levels to CBC measurements of hemoglobin levels with and without the use of a camera flash.
Figure 6B:
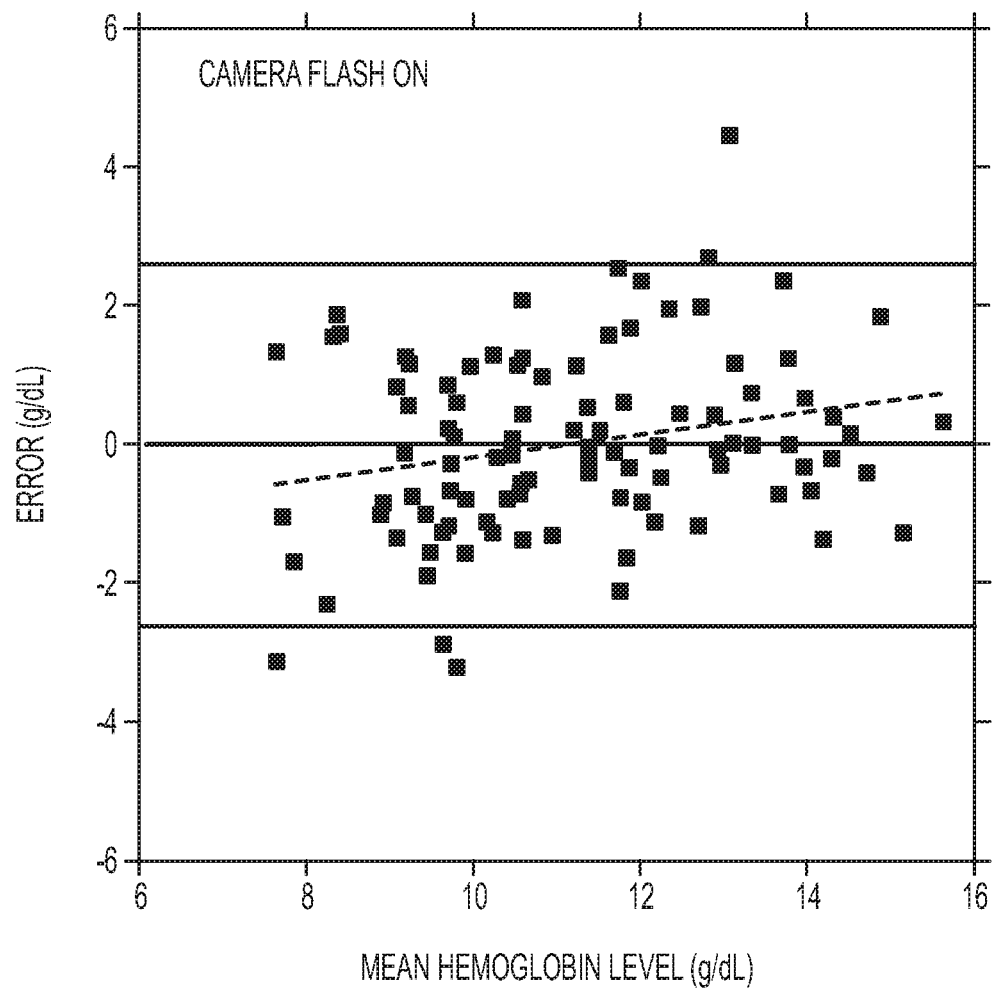
Figure 6C:
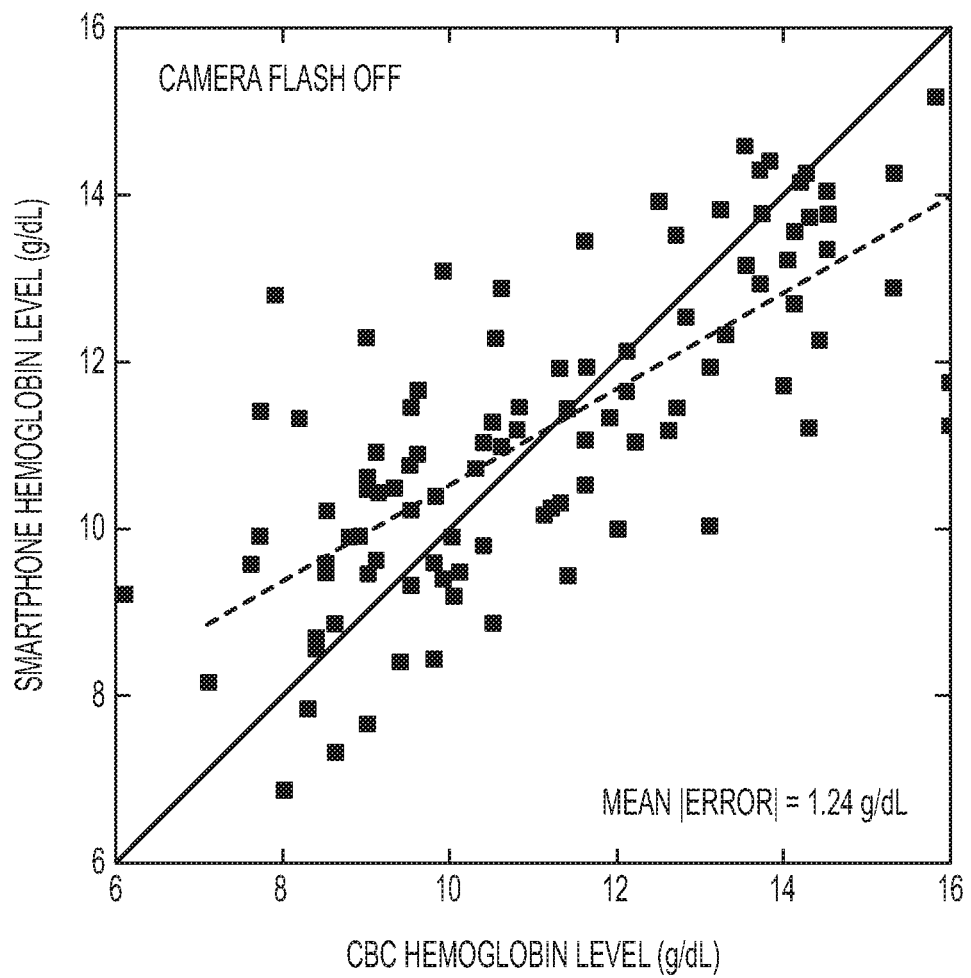
Figure 6D:
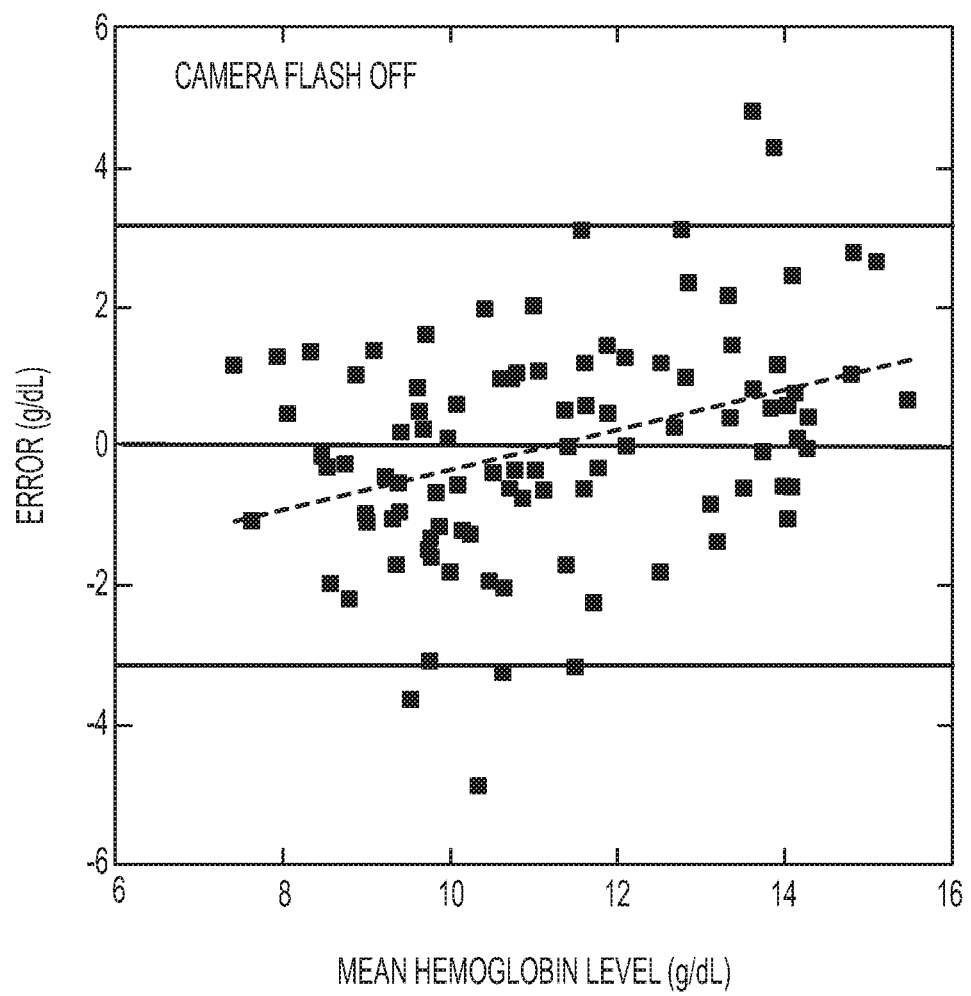
Figure 7A:
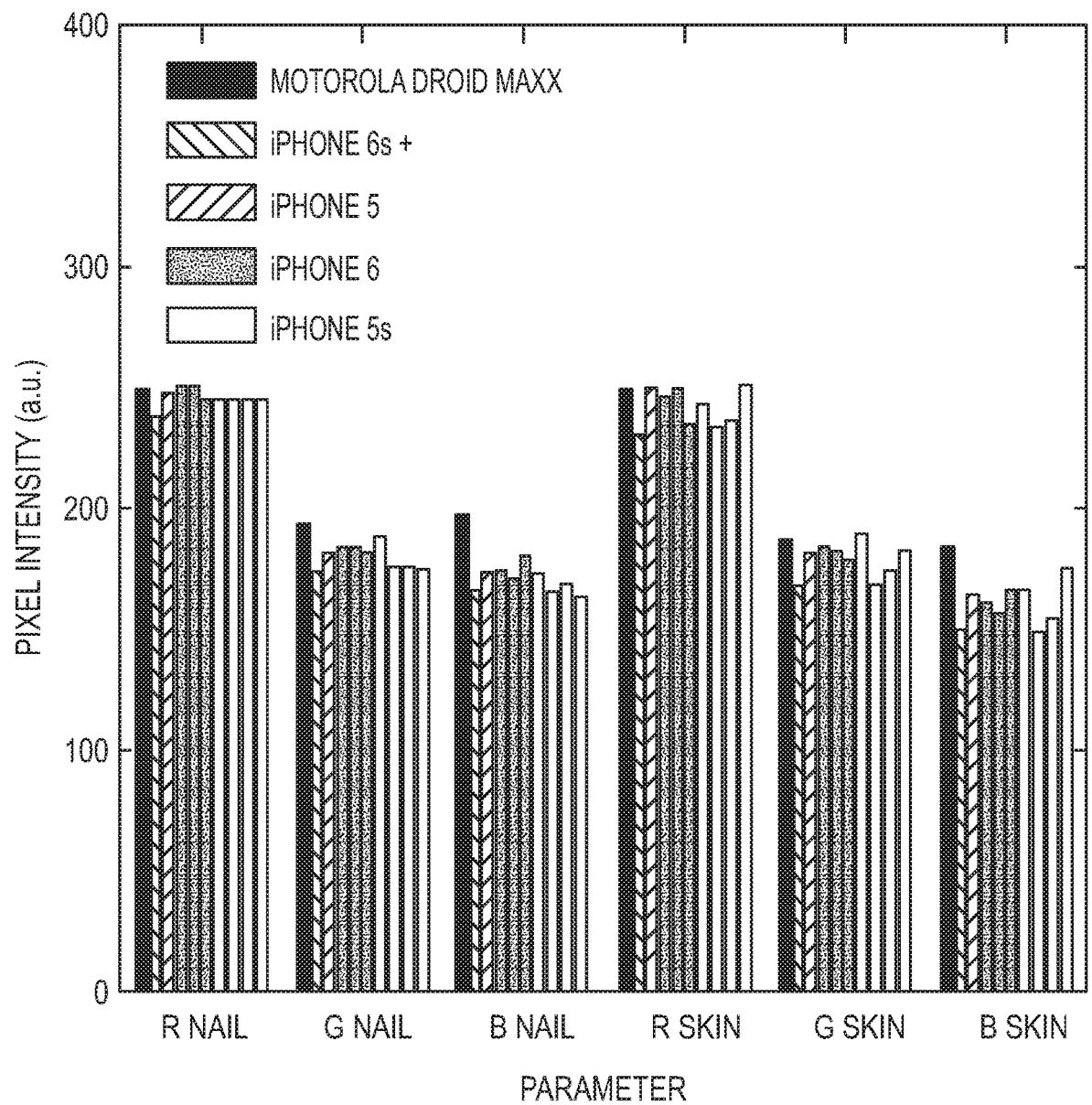
FIG. 7A-7B illustrate variability of color values of fingernails and skin color across different smartphones.
Figure 7B:
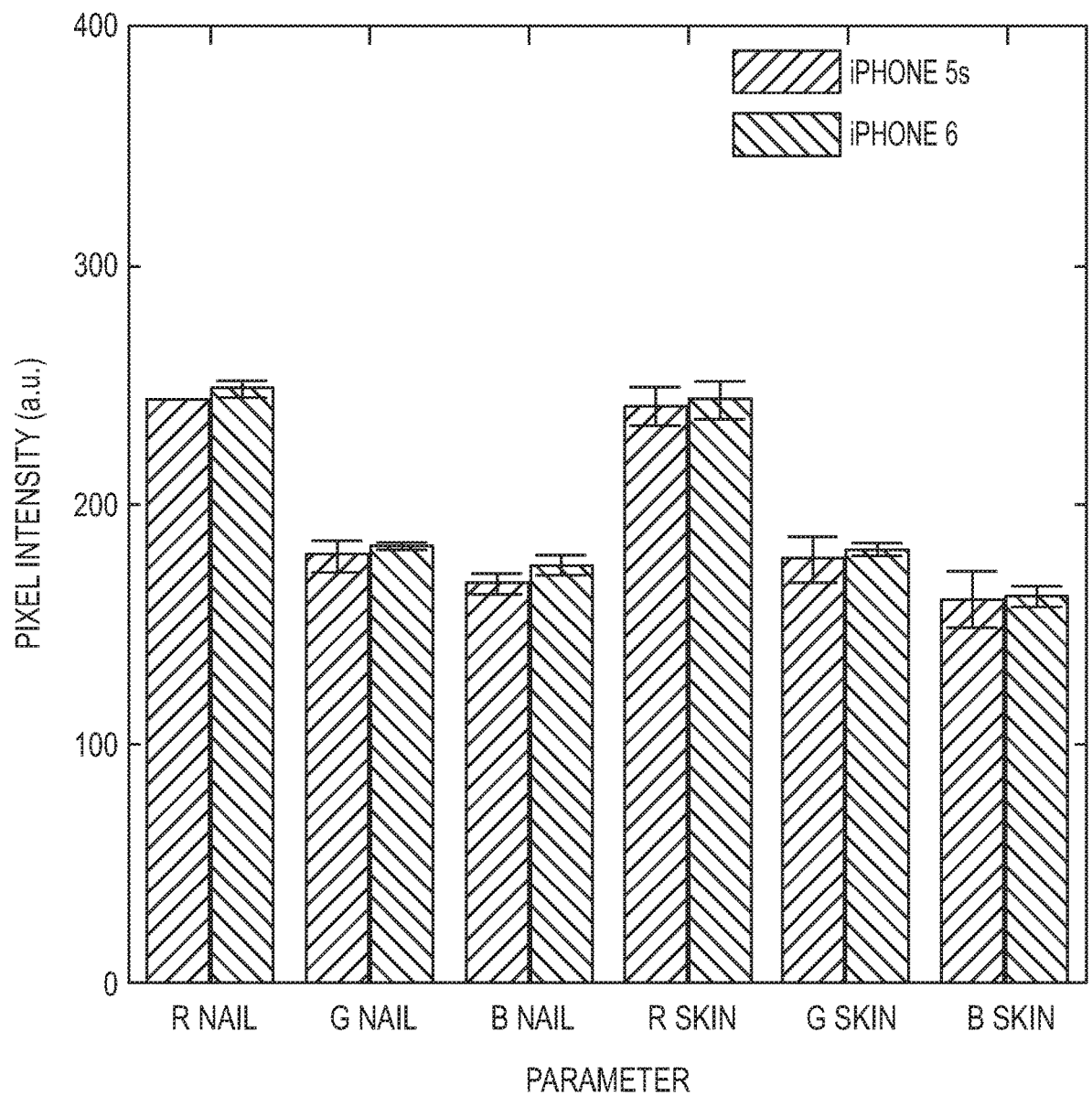

FIGS. 6A-6D illustrate comparisons of the hemoglobin image analysis with and without the use of a camera flash. Camera flash improves performance of the Hgb measurement algorithm. Use of the camera flash (FIGS. 6A-6B) leads to a decrease in the Hgb measurement error, as well as an increase in the correlation between the smartphone and CBC measurements, compared to when no camera flash is used (Flash on: r=0.23 Flash off: r=0.35) (FIGS. 6C-6D). Bland-Altman analysis shows a slight decrease in the correlation between the residual and the average Hgb level between the two tests when the camera flash is used. This indicates the presence of some experimental bias that is mitigated by use of the camera flash.

FIG. 7A-B illustrate variability of color values across different smartphones. The image analysis algorithm is camera-agnostic. As shown in FIG. 7A, RGB values of both fingernails and the skin of within a sample image taken with ten different models of smartphones remain consistent. As shown in FIG. 7B, there was no statistically significant difference between two different smartphone models developed by the same manufacturer (P>0.05). Statistical analysis was performed with a student's t-test assuming unequal variance. n=3 phones/model. Error bar reported as standard deviation.

FIG. 8 illustrates the variability of color values of different fingernails on the same individual. Color variability of fingernail beds is minimal across different fingers in the same individual. Color values in the red, green and blue channels were normalized to the second finger in each subject in order to compare color values from different subjects which were different due to variability within the study population. Fingers 3, 4, and 5 (the thumb was excluded from Hgb measurement) show little difference compared to finger 2. No statistically significant difference between color values across different fingers was found (p>0.30 in all cases). Statistical significance was determined via two-tailed Student's t-test assuming unequal variance.

FIG. 9 illustrates an improvement in accuracy in measured hemoglobin levels by adding a personalized calibration to the hemoglobin image analysis algorithm. Adding a personalized calibration step to generate a patient-specific algorithm further improves the accuracy of Hgb levels measurement and is ideal for chronic anemia patients. Healthy and chronically transfused anemic patients were monitored over four weeks (i.e. over the course of a therapeutic blood transfusion cycle). CBC Hgb levels were used in conjunction with the images to generate a personalized algorithm for each individual. As shown in FIG. 9, the patient-specific algorithms were used to measure Hgb levels over a subsequent blood transfusion cycle. This patient-specific calibration improved the average error of Hgb level measurements to within 0.41 g/dL of the CBC Hgb level. Bland-Altman analysis shows negligible experimental bias in the data. A random effects model is used to statistically confirm consistency of average Hgb level measurement error between individual subjects. The average error (solid black line) indicates the Hgb measurement of the smartphone app is negligibly biased. The dashed line represents the correlation (r=−0.24) between the residual error and the average of Hgb level measurements obtained from the CBC and the algorithm. The solid horizontal lines represent 95% limits of agreement (0.92 g/dL).

FIGS. 10A-B illustrate the effect of skin tone and background lighting on the error in measured hemoglobin levels. Background lighting and subject skin tone has minimal effect on Hgb measurement accuracy. Plotting measurement error against skin tone, shown in FIG. 10A, and background lighting, shown in FIG. 10B, reveals low and negligible correlation (r=0.13 and r=0.00 respectively) in either case. Dashed lines indicate linear fit between the measurement error and the tested parameter (skin tone and background lighting respectively). Inset images highlight a representative range of measured background skin tones and lighting conditions.

FIGS. 11A-D illustrate comparisons of accuracy of hemoglobin measurements by hematologists as compared to the hemoglobin image analysis algorithm. The app outperforms trained hematologists in hemoglobin measurement based on physical examination. Hematologists were able to estimate Hgb levels to within ±4.6 g/dL (95% limits of agreement), as shown in FIG. 11A, with an ROC of 0.63, shown in FIG. 11C. The app outperforms the hematologists in both respects with Hgb level accuracy measurement to within ±1.0 g/dL (95% limits of agreement), shown in FIG. 11B, and an ROC of 0.94, shown in FIG. 11D. The plots shown in FIGS. 11A and 110 represent the pooled results of 5 board certified hematologists estimating blood hemoglobin levels based on images of patients' fingernails.

Figure 12:
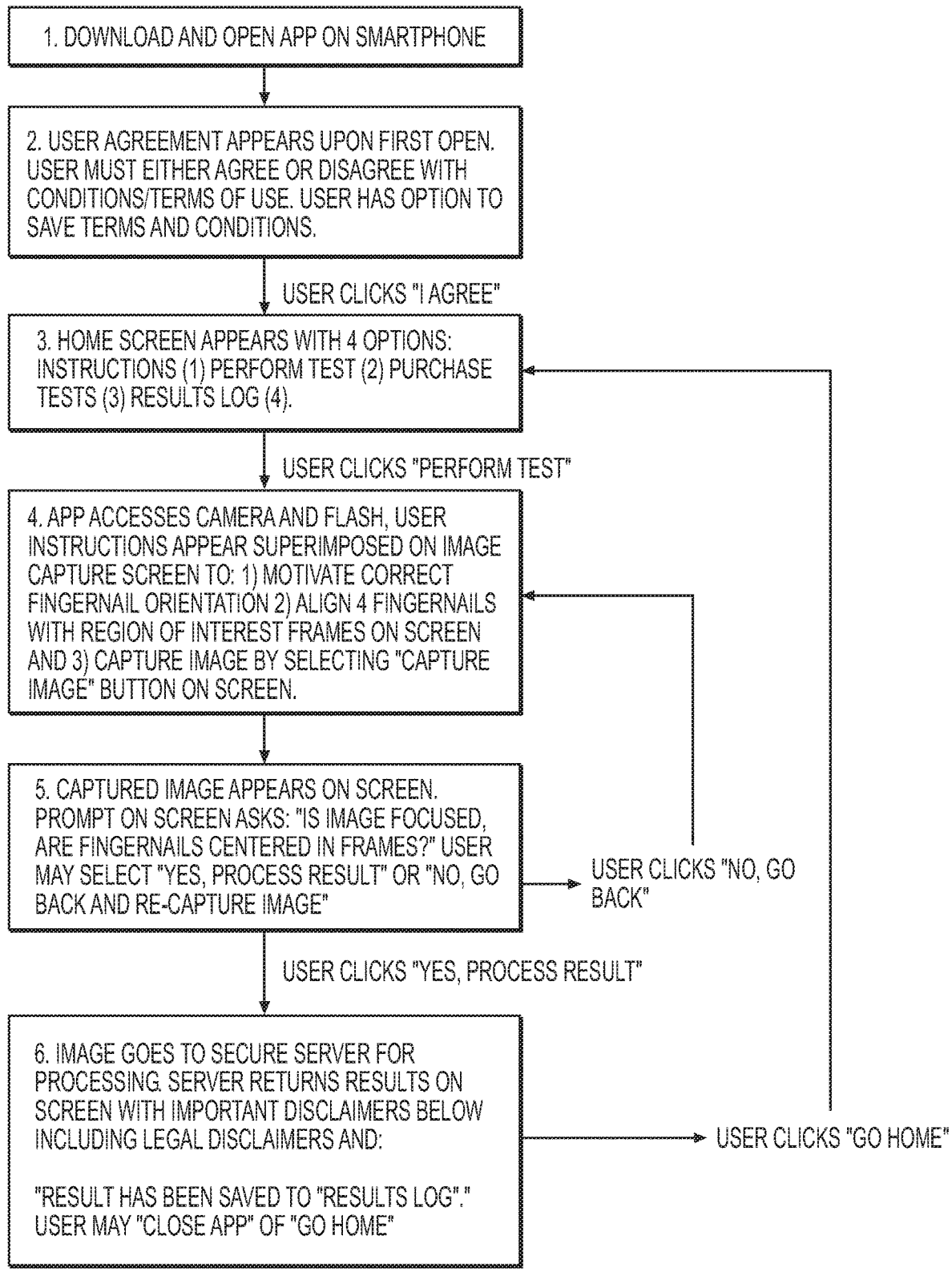
FIG. 12 illustrates a flowchart for a mobile application and a remote server for implementing the hemoglobin image analysis algorithm.

FIG. 12 illustrates a flowchart for a mobile application and a remote server for implementing the hemoglobin image analysis algorithm. The present systems and methods relate to non-invasive, on-demand diagnostics that may replace common blood-based laboratory tests requiring only patient-sourced electronic device photos. In various embodiments, the present on-demand system may allow users with any suitable electronic device (e.g. smartphone, tablet, etc.) to download an app and immediately detect anemia or other conditions. The app uses reflected light to produce an instantaneous result without additional equipment and therefore can enable on demand, self-testing.

The following description relates to one embodiment of the present disclosure as shown in FIG. 1, below. In one or more embodiments, an exemplary process begins with a user downloading an app onto their smartphone. In some embodiments, a user agreement may appear upon first opening the app. In particular embodiments, the user may agree or disagree with the conditions and terms of use and the user may have the option to save the terms and conditions.

According to one aspect of the present disclosure, if the user agrees to the terms and conditions, a home screen may appear with four options: 1) Instructions, 2) Perform Test, 3) Purchase Tests and 4) Results Log. However, as will be understood, in particular embodiments, the home screen may include additional, fewer, or different options.

In some embodiments, if the user selects "Perform Test," the app may access the camera and flash of a user's device and allow the user to take a self-image of his/her fingernail beds. Continuing with this embodiment, user instructions may appear superimposed onto the captured fingernail bed image instructing the user to: 1) motivate or assist the user in positioning each fingernail in the correct or optimal orientation; 2) align each fingernail with a region of interest frame on the screen; and 3) capture an image of each fingernail by selecting "Capture Image" (or the like) button on the screen. In some embodiments, the image of the one or more fingernails may be taken simultaneously. In some embodiments, the by way of example, the user instructions may instruct, align, and capture simultaneously four fingernails in four separate region of interest frames. In various embodiments, as the captured image of the fingernail beds appear on the screen, a prompt on the screen may ask "Is the image focused, are fingernails centered in frames?" (or the like). In one embodiment, the user may select either "Yes, process result" or "No, go back and re-capture image" (or a like prompt).

According to one aspect of the present disclosure, if the user clicks "No, go back" or a similar prompt, the user's app may access the camera to re-take the image of the fingernail beds. However, if the user clicks "Yes, process results" (or a like prompt), the system may send the image to a secure server for processing. In various embodiments, the server may display results on the screen with legal disclaimers that may state "Result has been saved to results log" (or the like) and the user may either close the app or click "Go Home" (or the like). In one or more embodiments, if the user selects "Go Home," the home screen may appear with four options: 1) Instructions, 2) Perform Test, 3) Purchase Tests and 4) Results Log and the process may continue herein. In some embodiments, if the user selects "Close App" (or the like), the app may hard close.

Figure 13:
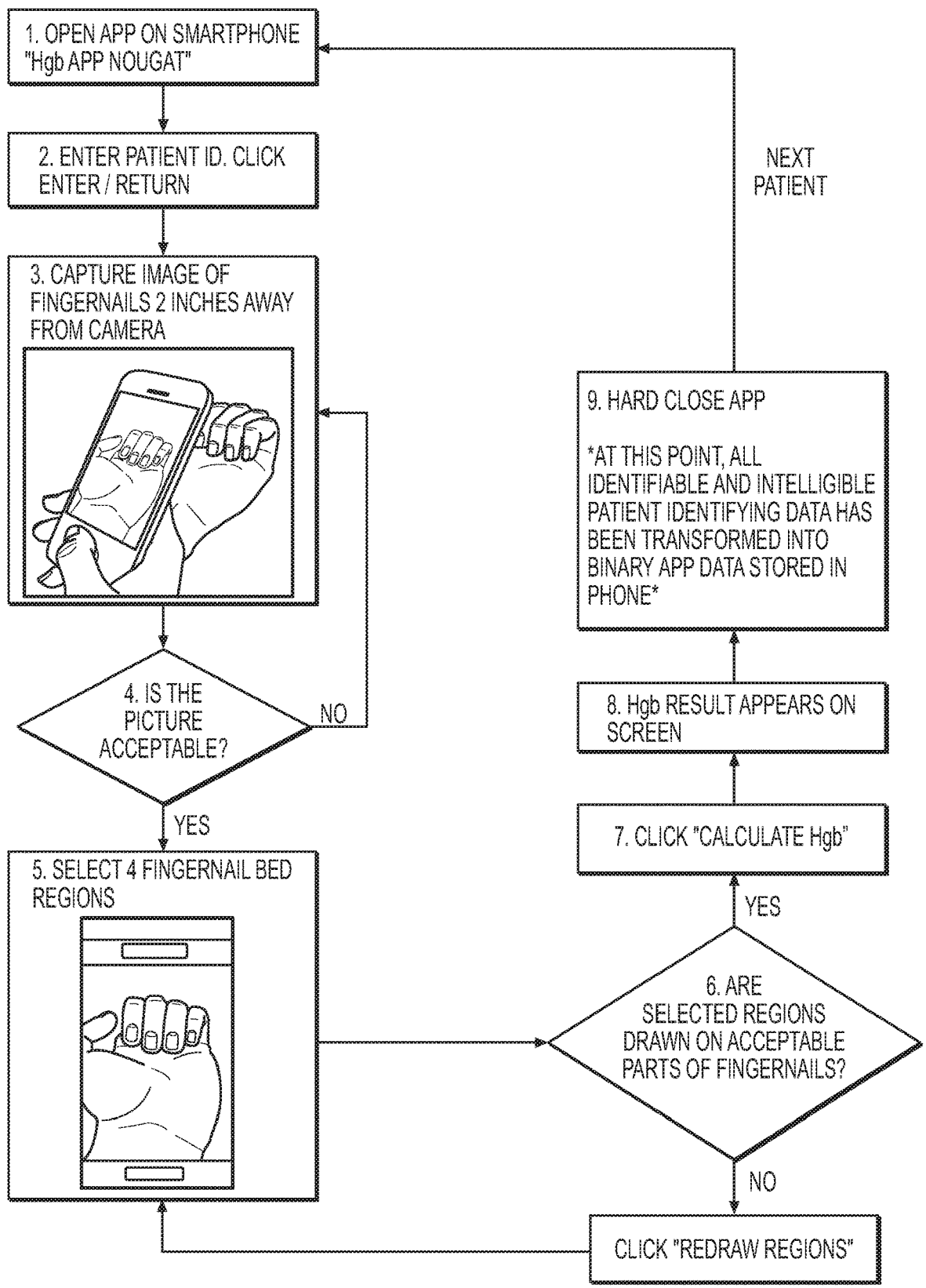
FIG. 13 is a flowchart of a mobile application for implementing the hemoglobin image analysis algorithm.

FIG. 13 is a flowchart of a mobile application for implementing the hemoglobin image analysis algorithm. The present systems and methods relate to non-invasive, on-demand diagnostics that may replace common blood-based laboratory tests requiring only patient-sourced electronic device photos. In various embodiments, the present on-demand system may allow users with any suitable electronic device (e.g. smartphone, tablet, etc.) to download an app and immediately detect anemia by calculating hemoglobin (Hgb) levels.

In one or more embodiments, the systems and methods begin with a user opening the app on his/her smartphone. In various embodiments, the user may enter a unique patient identification number and may click "Enter/Return" (or the like). In some embodiments, the user may capture an image of his/her fingernail beds of any suitable distance away from the camera. In particular embodiments, the user may capture an image approximately 6 inches away of his/her fingernail beds from the camera.

According to one aspect of the present disclosure, if the user selects "No" in responding to "Is the picture acceptable?" (or the like), then, the user may re-capture an image of the fingernail bed(s). However, if the user selects "Yes" in responding to "Is the picture acceptable?" (or the like), the system will select the four fingernail bed regions. In various embodiments, the system may ask "Are the selected regions drawn on acceptable parts of the fingernails?" (or the like). If "No," the user may click "Redraw Regions." In some embodiments, the user may manually select the regions by tapping on the image. If however, the user clicks "Yes," the system may calculate the Hgb levels.

For example, the system may calculate the Hgb levels by quantitatively analyzing pallor (e.g., skin tone) of the one or more fingernail beds in the one or more regions of interest to determine the user's approximate Hgb level. The system may measure the light reflected from the fingernail bed in the image to calculate the Hgb level. In some embodiments, the camera flash may be used to normalize variable background lighting conditions. This way, hemoglobin levels may be measured from a still image.

In some embodiments, the Hgb levels may be calculated by determining pixel intensity for each of the one or more regions of interest of the image. For example, color data may be extracted from each image of one or more fingernail beds. In some embodiments, the system may automatically exclude areas, such as leukonychia and/or camera flash reflection, from the one or more regions of interest.

The pixel intensity from color channels across each of the one or more regions of interest may then be averaged. In some embodiments, pixel intensity values outside a particular range may be excluded.

In some embodiments, the average pixel intensity from the color channels may be transformed into a value that correlates with the user's approximate Hgb level.

In some embodiments, the system may transform the average pixel intensity by determining metadata (e.g., camera settings) associated with the image and the mobile device and adjusting the value based on the metadata. In some embodiments, the system may transform the average pixel intensity by using linear regression to correct for variations in the average pixel intensity.

In some embodiments, the Hgb level results may appear on the screen. In some embodiments, the Hgb level results may be an approximate complete blood count (CBC) Hgb level.

In particular embodiments, at the point of the app hard closing all identifiable and intelligible patient identifying data may be transformed into the binary app data stored in the user's smartphone. In some embodiments, the data may be stored in a text file.

It should be appreciated that the logical operations described herein with respect to the various figures may be implemented (1) as a sequence of computer implemented acts or program modules (i.e., software) running on a computing device (e.g., the computing device described in FIG. 14), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 14:
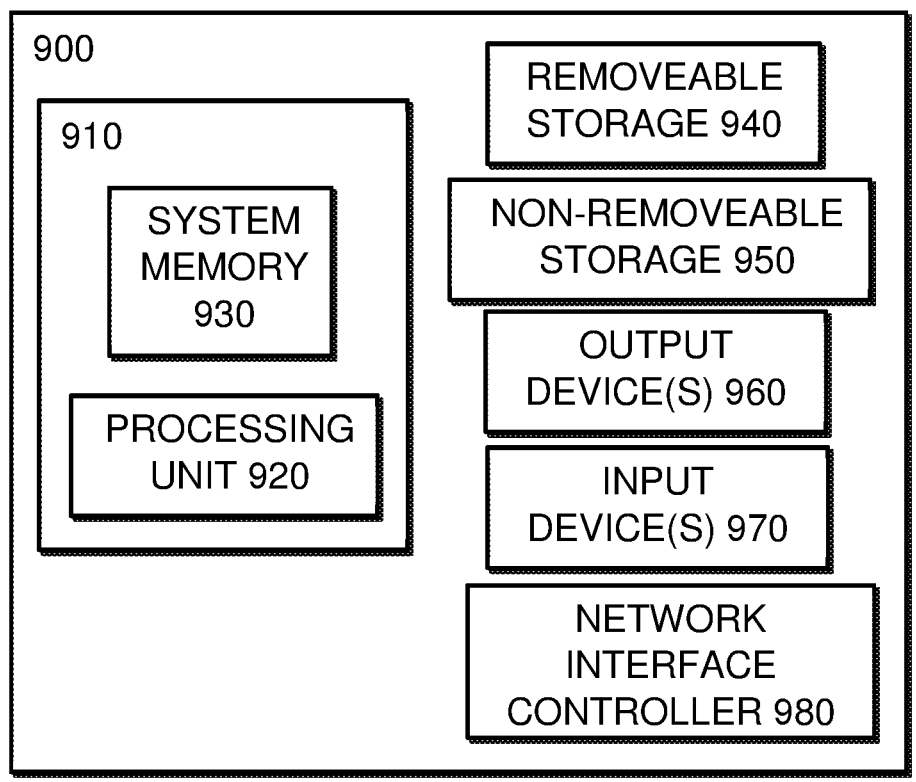
FIG. 14 illustrates an exemplary computer system suitable for implementing the several embodiments of the disclosure.

Referring to FIG. 14, an example computing device 900 upon which embodiments of the invention may be implemented is illustrated. For example, the smartphone, server, or other computer described herein may each be implemented as a computing device, such as computing device 900. It should be understood that the example computing device 900 is only one example of a suitable computing environment upon which embodiments of the invention may be implemented. Optionally, the computing device 900 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In an embodiment, the computing device 900 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computing device 900 to provide the functionality of a number of servers that is not directly bound to the number of computers in the computing device 900. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In its most basic configuration, computing device 900 typically includes at least one processing unit 920 and system memory 930. Depending on the exact configuration and type of computing device, system memory 930 may be volatile (such as random access memory (RAM)), non-volatile (such as read-only memory (ROM), flash memory, etc.), or some combination of the two. This most basic configuration is illustrated in FIG. 14 by dashed line 910. The processing unit 920 may be a standard programmable processor that performs arithmetic and logic operations necessary for operation of the computing device 900. While only one processing unit 920 is shown, multiple processors may be present. Thus, while instructions may be discussed as executed by a processor, the instructions may be executed simultaneously, serially, or otherwise executed by one or multiple processors. The computing device 900 may also include a bus or other communication mechanism for communicating information among various components of the computing device 900.

Computing device 900 may have additional features/functionality. For example, computing device 900 may include additional storage such as removable storage 940 and non-removable storage 950 including, but not limited to, magnetic or optical disks or tapes. Computing device 900 may also contain network connection(s) 980 that allow the device to communicate with other devices such as over the communication pathways described herein. The network connection(s) 980 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing device 900 may also have input device(s) 970 such as a keyboards, keypads, switches, dials, mice, track balls, touch screens, voice recognizers, card readers, paper tape readers, or other well-known input devices. Output device(s) 960 such as a printers, video monitors, liquid crystal displays (LCDs), touch screen displays, displays, speakers, etc. may also be included. The additional devices may be connected to the bus in order to facilitate communication of data among the components of the computing device 900. All these devices are well known in the art and need not be discussed at length here.

The processing unit 920 may be configured to execute program code encoded in tangible, computer-readable media. Tangible, computer-readable media refers to any media that is capable of providing data that causes the computing device 900 (i.e., a machine) to operate in a particular fashion. Various computer-readable media may be utilized to provide instructions to the processing unit 920 for execution. Example tangible, computer-readable media may include, but is not limited to, volatile media, non-volatile media, removable media and non-removable media implemented in any method or technology for storage of information such as computer readable instructions, data structures, program modules or other data. System memory 930, removable storage 940, and non-removable storage 950 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

In an example implementation, the processing unit 920 may execute program code stored in the system memory 930. For example, the bus may carry data to the system memory 930, from which the processing unit 920 receives and executes instructions. The data received by the system memory 930 may optionally be stored on the removable storage 940 or the non-removable storage 950 before or after execution by the processing unit 920.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Embodiments of the methods and systems may be described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

ADDITIONAL EXAMPLES

1. A method comprising: a method as shown and described herein.
2. The method of example 1, comprising each and every novel feature or combination of features shown and described herein.
3. A device as shown and described herein.
4. The device of example 3, comprising each and every novel feature or combination of features shown or described herein.

What is claimed is:

1. A system for analyzing an image for estimating hemoglobin levels, the system comprising at least one processor configured to:
    access a camera of a mobile device;
    force on a flash functionality of the camera to normalize variable background lighting conditions;
    capture, via the camera, an image of one or more fingernail beds of a user with the flash on, wherein:
        the camera automatically uses at least one lighting condition setting; and
        the mobile device automatically associates metadata with the image, the metadata comprising information about the flash and the at least one lighting condition setting;
    receive the image from the camera;
    receive an indication of one or more regions of interest on the image based, at least in part, on a user input to the mobile device, the one or more regions of interest at least partially including the one or more fingernail beds;
    determine pixel intensity for each of the one or more regions of interest;

average pixel intensity from color channels across each of the one or more regions of interest;

transform the average pixel intensity from the color channels into a value that correlates with the user's approximate hemoglobin (Hgb) level using machine learning to correct for variations in the average pixel intensity;

adjust the value based on the metadata associated with the image to compensate for the at least one lighting condition setting and the flash;

determine the user's approximate Hbg level from the image based on the adjusted value;

and output the user's approximate Hgb level to a display of the mobile device, wherein the Hgb level is used to monitor changes to the user's Hgb levels over time.

2. The system of claim 1, wherein the at least one processor is further configured to:

receive the indication of the one or more regions of interest; and automatically display a visual indication of the one or more regions of interest.

3. The system of claim 2, wherein the user input comprises the user tapping the image to indicate the one or more regions of interest.

4. The system of claim 2, wherein the visual indication of the one or more regions of interest comprise one or more boxes encompassing each of the one or more regions of interest.

5. The system of claim 1, wherein the one or more regions of interest include an area of approximately 10 $mm^2$.

6. The system of claim 1, wherein the one or more regions of interest consist of one or more portions of the one or more fingernail beds.

7. The system of claim 1, wherein the at least one processor is further configured to receive the indication of the one or more regions of interest automatically from a third-party computing system.

8. The system of claim 1, wherein the at least one processor is further configured to receive the indication of the one or more regions of interest automatically from a remote server.

9. The system of claim 8, wherein the remote server determines the one or more regions of interest via a machine learning algorithm.

10. The system of claim 1, wherein the at least one processor determines the one or more regions of interest via a machine learning algorithm.

11. The system of claim 1, wherein the system receives the image of the one or more fingernail beds of the user and quantitatively analyzes pallor of the one or more fingernail beds in the one or more regions of interest without the use of external hardware physically coupled to the system.

12. The system of claim 1, wherein the determining pixel intensity for each of the one or more regions of interest comprises extracting color data from the image.

13. The system of claim 1, wherein the at least one processor is further configured to exclude areas including leukonychia and/or camera flash reflection from the one or more regions of interest.

14. The system of claim 1, wherein the user's approximate Hgb level is an approximate complete blood count (CBC) Hgb level.

15. The system of claim 1, wherein the at least one processor is configured to save the user's approximate Hgb level in a text file.

16. The system of claim 1, wherein the at least one processor is configured to exclude pixel intensity values outside of a particular range when averaging pixel intensity for each of the one or more regions of interest.

17. The system of claim 1, wherein the at least one processor is further configured to confirm the image is acceptable by receiving a validation from the user.

18. The system of claim 1, wherein the metadata includes color management metadata including a white balance of the image.

19. The system of claim 1, wherein the approximate Hgb level is personally calibrated for the user based on at least one of: one or more previously determined Hgb levels or the user's medical history.

* * * * *